US010610211B2

(12) United States Patent
Callison et al.

(10) Patent No.: US 10,610,211 B2
(45) Date of Patent: Apr. 7, 2020

(54) FILAMENT ENGAGEMENT SYSTEM AND METHODS OF USE

(71) Applicant: Howmedica Osteonics Corp., Mahwah, NJ (US)

(72) Inventors: Ross Callison, Denver, CO (US); Kyle Craig Pilgeram, San Jose, CA (US); Charles McCartney, Denver, CO (US)

(73) Assignee: Howmedica Osteonics Corp., Mahwah, NJ (US)

( * ) Notice: Subject to any disclaimer, the term of this patent is extended or adjusted under 35 U.S.C. 154(b) by 1474 days.

(21) Appl. No.: 14/104,677

(22) Filed: Dec. 12, 2013

(65) Prior Publication Data

US 2015/0164497 A1 Jun. 18, 2015

(51) Int. Cl.
*A61B 17/04* (2006.01)
*A61B 17/06* (2006.01)

(52) U.S. Cl.
CPC ...... *A61B 17/0401* (2013.01); *A61B 17/0485* (2013.01); *A61B 17/0487* (2013.01); *A61B 2017/0406* (2013.01); *A61B 2017/0414* (2013.01); *A61B 2017/0445* (2013.01); *A61B 2017/0454* (2013.01); *A61B 2017/0458* (2013.01); *A61B 2017/0475* (2013.01);
(Continued)

(58) Field of Classification Search
CPC ............ A61B 17/0401; A61B 17/0485; A61B 17/0487; A61B 17/0446; A61B 2017/0406; A61B 2017/0414; A61B 2017/0445; A61B 2017/0454; A61B 2017/0458; A61B 2017/0475; A61B 2017/0477; A61B 2017/00336

USPC ........................................................ 606/232
See application file for complete search history.

(56) References Cited

U.S. PATENT DOCUMENTS 749,624 A 1/1904 McCullough
1,308,798 A 7/1919 Masland
(Continued)

FOREIGN PATENT DOCUMENTS

DE 3131496 A1 2/1983
DE 4231101 A1 3/1994
(Continued)

OTHER PUBLICATIONS

International Search Report and Written Opinion for Application No. PCT/US2014/069087 dated Jun. 17, 2015.
(Continued)

*Primary Examiner* — Ryan J. Severson
*Assistant Examiner* — Socrates L Boutsikaris
(74) *Attorney, Agent, or Firm* — Lerner, David, Littenberg, Krumholz & Mentlik, LLP

(57) ABSTRACT

A system for securing a length of filament in working communication with tissue. The system includes a first filamentary sleeve having a length along a longitudinal axis and a passageway therethrough. The passageway is dimensioned to allow slidable movement therein of a length of filament. Also included within the system is and a filament engagement device that includes a pathway. The pathway has a first configuration and second configuration, wherein a portion of the length of filament is slidable within the pathway when the pathway is in the first configuration and is restricted from sliding when the pathway is in the second configuration.

9 Claims, 24 Drawing Sheets

(52) U.S. Cl.
CPC ............... *A61B 2017/0477* (2013.01); *A61B 2017/06185* (2013.01)

(56) References Cited

U.S. PATENT DOCUMENTS

| | | |
|---|---|---|
| 1,624,530 A | 4/1927 | Caruso |
| 2,073,903 A | 3/1937 | O'Neil |
| 2,250,434 A | 7/1941 | Dugaw |
| 2,267,925 A | 12/1941 | Johnston |
| 2,382,019 A | 8/1945 | Miller |
| 2,461,947 A | 2/1949 | Weber |
| 2,494,229 A | 1/1950 | Collison |
| 2,515,365 A | 7/1950 | Zublin |
| 2,547,571 A | 4/1951 | Ettinger |
| 2,773,672 A | 12/1956 | Holmes et al. |
| 2,808,632 A | 10/1957 | Cline |
| 2,833,284 A | 5/1958 | Springer |
| 3,384,085 A | 5/1968 | Hall |
| 3,461,875 A | 8/1969 | Hall |
| 3,554,192 A | 1/1971 | Isberner |
| 3,580,256 A | 5/1971 | Wilkinson et al. |
| 3,608,095 A | 9/1971 | Barry |
| 3,659,597 A | 5/1972 | Wolfers |
| 3,750,671 A | 8/1973 | Hedrick |
| 3,810,456 A | 5/1974 | Karman |
| 3,845,772 A | 11/1974 | Smith |
| 3,867,932 A | 2/1975 | Huene |
| 3,892,232 A | 7/1975 | Neufeld |
| 3,976,079 A | 8/1976 | Samuels et al. |
| 4,212,569 A | 7/1980 | Andersson et al. |
| 4,265,231 A | 5/1981 | Scheller, Jr. et al. |
| 4,328,839 A | 5/1982 | Lyons et al. |
| 4,483,562 A | 11/1984 | Schoolman |
| 4,489,446 A | 12/1984 | Reed |
| 4,541,423 A | 9/1985 | Barber |
| 4,594,033 A | 6/1986 | Peetz et al. |
| 4,605,347 A | 8/1986 | Jodock et al. |
| 4,608,972 A | 9/1986 | Small |
| 4,611,515 A | 9/1986 | Marbourg, Jr. |
| 4,635,738 A | 1/1987 | Schillinger et al. |
| 4,646,738 A | 3/1987 | Trott |
| 4,706,659 A | 11/1987 | Matthews et al. |
| 4,728,231 A | 3/1988 | Kunimori et al. |
| 4,741,330 A | 5/1988 | Hayhurst |
| 4,748,872 A | 6/1988 | Brown |
| 4,751,922 A | 6/1988 | DiPietropolo |
| 4,781,182 A | 11/1988 | Purnell et al. |
| 4,823,780 A | 4/1989 | Odensten et al. |
| 4,842,451 A | 6/1989 | Dugger |
| 4,863,471 A | 9/1989 | Mansat |
| 4,872,451 A | 10/1989 | Moore et al. |
| 4,946,462 A | 8/1990 | Watanabe |
| 5,002,546 A | 3/1991 | Romano |
| 5,007,911 A | 4/1991 | Baker |
| 5,021,059 A | 6/1991 | Kensey et al. |
| 5,030,219 A | 7/1991 | Matsen, III et al. |
| 5,037,422 A | 8/1991 | Hayhurst et al. |
| 5,037,423 A | 8/1991 | Kenna |
| 5,061,277 A | 10/1991 | Carpentier et al. |
| 5,064,431 A | 11/1991 | Gilbertson et al. |
| 5,122,134 A | 6/1992 | Borzone et al. |
| 5,123,914 A | 6/1992 | Cope |
| 5,133,720 A | 7/1992 | Greenberg |
| 5,139,520 A | 8/1992 | Rosenberg |
| 5,141,520 A | 8/1992 | Goble et al. |
| 5,163,940 A | 11/1992 | Bourque |
| 5,165,494 A | 11/1992 | Barr |
| 5,186,268 A | 2/1993 | Clegg |
| 5,190,548 A | 3/1993 | Davis |
| 5,203,595 A | 4/1993 | Borzone et al. |
| 5,203,787 A | 4/1993 | Noblitt et al. |
| RE34,293 E | 6/1993 | Goble et al. |
| 5,234,435 A | 8/1993 | Seagrave, Jr. |
| 5,259,846 A | 11/1993 | Granger et al. |
| 5,269,785 A | 12/1993 | Bonutti |
| 5,269,809 A | 12/1993 | Hayhurst et al. |
| 5,273,380 A | 12/1993 | Musacchia |
| 5,300,077 A | 4/1994 | Howell |
| 5,314,429 A | 5/1994 | Goble |
| 5,320,115 A | 6/1994 | Kenna |
| 5,320,626 A | 6/1994 | Schmieding |
| 5,324,308 A | 6/1994 | Pierce |
| 5,350,383 A | 9/1994 | Schmieding et al. |
| RE34,762 E | 10/1994 | Goble et al. |
| 5,374,269 A | 12/1994 | Rosenberg |
| 5,385,567 A | 1/1995 | Goble |
| 5,391,170 A | 2/1995 | McGuire et al. |
| 5,391,171 A | 2/1995 | Schmieding |
| RE34,871 E | 3/1995 | McGuire et al. |
| 5,395,188 A | 3/1995 | Bailey et al. |
| 5,403,317 A | 4/1995 | Bonutti |
| 5,403,348 A | 4/1995 | Bonutti |
| 5,405,359 A | 4/1995 | Pierce |
| 5,409,494 A | 4/1995 | Morgan |
| 5,417,691 A | 5/1995 | Hayhurst |
| 5,423,824 A | 6/1995 | Akerfeldt et al. |
| 5,423,860 A | 6/1995 | Lizardi et al. |
| 5,437,675 A | 8/1995 | Wilson |
| 5,437,677 A | 8/1995 | Shearer et al. |
| 5,441,502 A | 8/1995 | Bartlett |
| 5,443,482 A | 8/1995 | Stone et al. |
| 5,458,604 A | 10/1995 | Schmieding |
| 5,464,407 A | 11/1995 | McGuire |
| 5,464,425 A | 11/1995 | Skiba |
| 5,464,426 A | 11/1995 | Bonutti |
| 5,466,243 A | 11/1995 | Schmieding et al. |
| 5,472,452 A | 12/1995 | Trott |
| 5,486,197 A | 1/1996 | Le et al. |
| 5,488,761 A | 2/1996 | Leone |
| 5,496,348 A | 3/1996 | Bonutti |
| 5,505,736 A | 4/1996 | Reimels et al. |
| 5,520,693 A | 5/1996 | McGuire et al. |
| 5,520,700 A | 5/1996 | Beyar et al. |
| 5,522,846 A | 6/1996 | Bonutti |
| 5,527,316 A | 6/1996 | Stone et al. |
| 5,527,343 A | 6/1996 | Bonutti |
| 5,529,580 A | 6/1996 | Kusunoki et al. |
| 5,531,759 A | 7/1996 | Kensey et al. |
| 5,534,012 A | 7/1996 | Bonutti |
| 5,540,703 A | 7/1996 | Barker, Jr. et al. |
| 5,545,178 A | 8/1996 | Kensey et al. |
| 5,548,862 A | 8/1996 | Curtis |
| 5,569,269 A | 10/1996 | Hart et al. |
| 5,569,306 A | 10/1996 | Thal |
| 5,570,706 A | 11/1996 | Howell |
| 5,571,111 A | 11/1996 | Aboczky |
| 5,573,542 A | 11/1996 | Stevens |
| 5,575,819 A | 11/1996 | Amis |
| 5,584,695 A | 12/1996 | Lal Sachdeva et al. |
| 5,584,835 A | 12/1996 | Greenfield |
| 5,601,557 A | 2/1997 | Hayhurst |
| 5,601,561 A | 2/1997 | Terry et al. |
| 5,618,314 A | 4/1997 | Harwin et al. |
| 5,645,545 A | 7/1997 | Bryant |
| 5,645,589 A | 7/1997 | Li |
| 5,647,874 A | 7/1997 | Hayhurst |
| 5,649,963 A | 7/1997 | McDevitt |
| 5,658,313 A | 8/1997 | Thal |
| 5,662,658 A | 9/1997 | Wenstrom, Jr. |
| 5,665,110 A | 9/1997 | Chervitz et al. |
| 5,665,111 A | 9/1997 | Ray et al. |
| 5,665,112 A | 9/1997 | Thal |
| 5,667,509 A | 9/1997 | Westin |
| 5,674,279 A | 10/1997 | Wright et al. |
| 5,681,320 A | 10/1997 | McGuire |
| 5,681,352 A | 10/1997 | Clancy, III et al. |
| 5,683,401 A | 11/1997 | Schmieding et al. |
| 5,683,418 A | 11/1997 | Luscombe et al. |
| 5,683,419 A | 11/1997 | Thal |
| 5,690,676 A | 11/1997 | DiPoto et al. |
| 5,690,677 A | 11/1997 | Schmieding et al. |
| 5,695,513 A | 12/1997 | Johnson et al. |
| 5,699,657 A | 12/1997 | Paulson |
| 5,702,397 A | 12/1997 | Goble et al. |

(56) References Cited

U.S. PATENT DOCUMENTS

| | | |
|---|---|---|
| 5,709,708 A | 1/1998 | Thal |
| 5,713,905 A | 2/1998 | Goble et al. |
| 5,716,397 A | 2/1998 | Myers |
| 5,718,717 A | 2/1998 | Bonutti |
| 5,720,765 A | 2/1998 | Thal |
| 5,725,541 A | 3/1998 | Anspach, III et al. |
| 5,725,557 A | 3/1998 | Gatturna et al. |
| 5,728,136 A | 3/1998 | Thal |
| 5,732,606 A | 3/1998 | Chiang |
| 5,733,306 A | 3/1998 | Bonutti |
| 5,733,307 A | 3/1998 | Dinsdale |
| 5,749,899 A | 5/1998 | Bardin et al. |
| 5,755,724 A | 5/1998 | Yoon |
| 5,755,731 A | 5/1998 | Grinberg |
| 5,766,221 A | 6/1998 | Benderev et al. |
| 5,782,862 A | 7/1998 | Bonutti |
| 5,782,864 A | 7/1998 | Lizardi |
| 5,782,866 A | 7/1998 | Wenstrom, Jr. |
| 5,797,918 A | 8/1998 | McGuire et al. |
| 5,810,825 A | 9/1998 | Huebner |
| 5,814,056 A | 9/1998 | Prosst et al. |
| 5,836,953 A | 11/1998 | Yoon |
| 5,851,208 A | 12/1998 | Trott |
| 5,885,294 A | 3/1999 | Pedlick et al. |
| 5,888,034 A | 3/1999 | Greenberg |
| 5,891,168 A | 4/1999 | Thal |
| 5,897,574 A | 4/1999 | Bonutti |
| 5,906,626 A | 5/1999 | Carrillo |
| 5,921,986 A | 7/1999 | Bonutti |
| 5,928,244 A | 7/1999 | Tovey et al. |
| 5,941,139 A | 8/1999 | Vodehnal |
| 5,948,002 A | 9/1999 | Banutti |
| 5,951,559 A | 9/1999 | Burkhart |
| 5,968,078 A | 10/1999 | Grotz |
| 5,980,539 A | 11/1999 | Kontos |
| 5,980,558 A | 11/1999 | Wiley |
| 5,980,559 A | 11/1999 | Bonutti |
| 5,989,252 A | 11/1999 | Fumex |
| 5,993,451 A | 11/1999 | Burkhart |
| 5,997,541 A | 12/1999 | Schenk |
| 6,007,566 A | 12/1999 | Wenstrom, Jr. |
| 6,007,567 A | 12/1999 | Bonutti |
| 6,010,515 A | 1/2000 | Swain et al. |
| 6,010,525 A | 1/2000 | Bonutti et al. |
| 6,019,767 A | 2/2000 | Howell |
| 6,024,758 A | 2/2000 | Thal |
| 6,030,406 A | 2/2000 | Davis et al. |
| 6,045,574 A | 4/2000 | Thal |
| 6,053,922 A | 4/2000 | Krause et al. |
| 6,068,642 A | 5/2000 | Johnson et al. |
| 6,077,292 A | 6/2000 | Bonutti |
| 6,120,511 A | 9/2000 | Chan |
| 6,143,017 A | 11/2000 | Thal |
| 6,146,385 A | 11/2000 | Torrie et al. |
| 6,152,949 A | 11/2000 | Bonutti |
| 6,156,039 A | 12/2000 | Thal |
| 6,156,056 A | 12/2000 | Kearns et al. |
| 6,159,234 A | 12/2000 | Bonutti et al. |
| 6,183,461 B1 | 2/2001 | Matsuura et al. |
| 6,187,011 B1 | 2/2001 | Torrie |
| 6,189,422 B1 | 2/2001 | Stihl |
| 6,210,415 B1 | 4/2001 | Bester |
| 6,224,608 B1 | 5/2001 | Ciccolella et al. |
| 6,245,081 B1 | 6/2001 | Bowman et al. |
| 6,254,604 B1 | 7/2001 | Howell |
| 6,306,138 B1 | 10/2001 | Clark et al. |
| 6,306,159 B1 | 10/2001 | Schwartz et al. |
| 6,343,482 B1 | 2/2002 | Endo et al. |
| 6,352,538 B2 | 3/2002 | McGuire et al. |
| 6,358,253 B1 | 3/2002 | Torrie et al. |
| 6,419,678 B1 | 7/2002 | Asfora |
| 6,419,684 B1 | 7/2002 | Heisler et al. |
| 6,436,100 B1 | 8/2002 | Berger |
| 6,436,124 B1 | 8/2002 | Anderson et al. |
| 6,440,138 B1 | 8/2002 | Reiley et al. |
| 6,440,141 B1 | 8/2002 | Philippon |
| 6,447,518 B1 | 9/2002 | Krause et al. |
| 6,464,713 B2 | 10/2002 | Bonutti |
| 6,475,230 B1 | 11/2002 | Bonutti et al. |
| 6,478,800 B1 | 11/2002 | Fraser et al. |
| 6,485,504 B1 | 11/2002 | Johnson et al. |
| 6,494,272 B1 | 12/2002 | Eppink et al. |
| 6,500,195 B2 | 12/2002 | Bonutti |
| RE37,963 E | 1/2003 | Thal |
| 6,508,830 B2 | 1/2003 | Steiner |
| 6,511,498 B1 | 1/2003 | Fumex |
| 6,517,578 B2 | 2/2003 | Hein |
| 6,544,281 B2 | 4/2003 | ElAttrache et al. |
| 6,558,386 B1 | 5/2003 | Cragg |
| 6,558,390 B2 | 5/2003 | Cragg |
| 6,569,187 B1 | 5/2003 | Bonutti et al. |
| 6,572,635 B1 | 6/2003 | Bonutti |
| 6,575,979 B1 | 6/2003 | Cragg |
| 6,610,080 B2 | 8/2003 | Morgan |
| 6,635,073 B2 | 10/2003 | Bonutti |
| 6,638,279 B2 | 10/2003 | Bonutti |
| 6,638,283 B2 | 10/2003 | Thal |
| 6,641,597 B2 | 11/2003 | Burkhart et al. |
| 6,660,023 B2 | 12/2003 | McDevitt et al. |
| 6,712,822 B2 | 3/2004 | Re et al. |
| 6,716,234 B2 | 4/2004 | Grafton et al. |
| 6,740,090 B1 | 5/2004 | Cragg et al. |
| 6,780,188 B2 | 8/2004 | Clark et al. |
| 6,790,210 B1 | 9/2004 | Cragg et al. |
| 6,805,697 B1 | 10/2004 | Helm et al. |
| 6,824,552 B2 | 11/2004 | Robison et al. |
| 6,830,570 B1 | 12/2004 | Frey et al. |
| 6,863,672 B2 | 3/2005 | Reiley et al. |
| 6,878,150 B2 | 4/2005 | McGuire et al. |
| 6,887,259 B2 | 5/2005 | Lizardi |
| 6,893,445 B1 | 5/2005 | Revie et al. |
| 6,899,716 B2 | 5/2005 | Cragg |
| 6,921,403 B2 | 7/2005 | Cragg et al. |
| 6,923,811 B1 | 8/2005 | Carl et al. |
| 6,923,814 B1 | 8/2005 | Hildebrand et al. |
| 6,936,052 B2 | 8/2005 | Gellman et al. |
| 6,955,683 B2 | 10/2005 | Bonutti |
| 6,960,214 B2 | 11/2005 | Burkinshaw |
| 6,991,636 B2 | 1/2006 | Rose |
| 6,994,719 B2 | 2/2006 | Grafton |
| 6,994,725 B1 | 2/2006 | Goble |
| 6,995,683 B2 | 2/2006 | Smithson et al. |
| 7,008,431 B2 | 3/2006 | Simonson |
| 7,025,770 B2 | 4/2006 | McGuire et al. |
| 7,029,490 B2 | 4/2006 | Grafton et al. |
| 7,048,754 B2 | 5/2006 | Martin et al. |
| 7,060,073 B2 | 6/2006 | Frey et al. |
| 7,067,132 B2 | 6/2006 | Grabstein et al. |
| 7,077,863 B2 | 7/2006 | Schmieding et al. |
| 7,087,058 B2 | 8/2006 | Cragg |
| 7,087,073 B2 | 8/2006 | Bonutti |
| 7,204,839 B2 | 4/2007 | Dreyfuss et al. |
| 7,217,279 B2 | 5/2007 | Reese |
| 7,217,290 B2 | 5/2007 | Bonutti |
| 7,235,091 B2 | 6/2007 | Thornes |
| 7,241,297 B2 | 7/2007 | Shaolian et al. |
| 7,258,692 B2 | 8/2007 | Thelen et al. |
| 7,261,016 B2 | 8/2007 | Miller |
| 7,309,338 B2 | 12/2007 | Cragg |
| 7,326,215 B2 | 2/2008 | Myers et al. |
| 7,331,263 B2 | 2/2008 | Erickson et al. |
| 7,381,213 B2 | 6/2008 | Lizardi |
| 7,488,322 B2 | 2/2009 | Brunnett et al. |
| 7,488,329 B2 | 2/2009 | Thelen et al. |
| 7,494,490 B2 | 2/2009 | Justin |
| 7,500,977 B2 | 3/2009 | Assell et al. |
| 7,503,920 B2 | 3/2009 | Siegal |
| 7,520,898 B2 | 4/2009 | Re et al. |
| 7,563,266 B2 | 7/2009 | Camino et al. |
| 7,578,836 B2 | 8/2009 | Justin et al. |
| 7,585,300 B2 | 9/2009 | Cha |
| 7,601,155 B2 | 10/2009 | Petersen |
| 7,601,165 B2 | 10/2009 | Stone |
| 7,604,636 B1 | 10/2009 | Walters et al. |

(56) References Cited

U.S. PATENT DOCUMENTS

| | | |
|---|---|---|
| 7,608,098 B1 | 10/2009 | Stone et al. |
| 7,611,521 B2 | 11/2009 | Lubbers et al. |
| 7,621,912 B2 | 11/2009 | Harms et al. |
| 7,621,940 B2 | 11/2009 | Harms et al. |
| 7,651,509 B2 | 1/2010 | Bojarski et al. |
| 7,651,515 B2 | 1/2010 | Mack et al. |
| 7,658,751 B2 | 2/2010 | Stone et al. |
| 7,666,189 B2 | 2/2010 | Gerber et al. |
| 7,678,134 B2 | 3/2010 | Schmieding et al. |
| 7,749,250 B2 | 7/2010 | Stone et al. |
| 7,776,049 B1 | 8/2010 | Curran et al. |
| 7,803,173 B2 | 9/2010 | Burkhart et al. |
| 7,857,830 B2 | 12/2010 | Stone et al. |
| 7,875,057 B2 | 1/2011 | Cook et al. |
| 7,875,058 B2 | 1/2011 | Holmes, Jr. |
| 7,879,037 B2 | 2/2011 | Brunnett et al. |
| 7,892,256 B2 | 2/2011 | Grafton et al. |
| 7,901,431 B2 | 3/2011 | Shurnas |
| 7,905,903 B2 | 3/2011 | Stone et al. |
| 7,905,904 B2 | 3/2011 | Stone et al. |
| 7,909,851 B2 | 3/2011 | Stone et al. |
| 7,914,539 B2 | 3/2011 | Stone et al. |
| 7,918,874 B2 | 4/2011 | Siegal |
| 7,959,650 B2 | 6/2011 | Kaiser et al. |
| 7,981,117 B2 | 7/2011 | Newton et al. |
| 7,981,140 B2 | 7/2011 | Burkhart |
| 7,993,369 B2 | 8/2011 | Dreyfuss |
| 8,002,733 B2 | 8/2011 | Kraft et al. |
| 8,043,253 B2 | 10/2011 | Kraft et al. |
| 8,057,500 B2 | 11/2011 | Mitusina |
| 8,088,130 B2 | 1/2012 | Kaiser et al. |
| 8,114,088 B2 | 2/2012 | Miller |
| 8,118,836 B2 | 2/2012 | Denham et al. |
| 8,123,750 B2 | 2/2012 | Norton et al. |
| 8,128,640 B2 | 3/2012 | Harris et al. |
| 8,128,658 B2 | 3/2012 | Kaiser et al. |
| 8,128,669 B2 | 3/2012 | Bonutti |
| 8,133,231 B2 | 3/2012 | Martinek et al. |
| 8,137,382 B2 | 3/2012 | Denham et al. |
| 8,147,514 B2 | 4/2012 | Bonutti |
| 8,162,997 B2 | 4/2012 | Struhl |
| 8,172,846 B2 | 5/2012 | Brunnett et al. |
| 8,231,654 B2 | 7/2012 | Kaiser et al. |
| 8,231,674 B2 | 7/2012 | Albertorio et al. |
| 8,241,305 B2 | 8/2012 | Stone |
| 8,267,959 B2 | 9/2012 | Fallman |
| 8,273,106 B2 | 9/2012 | Stone et al. |
| 8,292,921 B2 | 10/2012 | Stone et al. |
| 8,298,262 B2 | 10/2012 | Stone et al. |
| 8,303,604 B2 | 11/2012 | Stone et al. |
| 8,317,825 B2 | 11/2012 | Stone |
| 8,337,525 B2 | 12/2012 | Stone et al. |
| 8,361,113 B2 | 1/2013 | Stone et al. |
| 8,398,678 B2 | 3/2013 | Baker et al. |
| 8,439,976 B2 | 5/2013 | Albertorio et al. |
| 8,591,578 B2 | 11/2013 | Albertorio et al. |
| 8,623,051 B2 | 1/2014 | Bojarski et al. |
| 8,663,324 B2 | 3/2014 | Schmieding et al. |
| 8,801,800 B2 | 8/2014 | Bagga et al. |
| 8,814,905 B2 | 8/2014 | Sengun et al. |
| 8,821,543 B2 | 9/2014 | Hernandez et al. |
| 8,821,544 B2 | 9/2014 | Sengun et al. |
| 8,821,545 B2 | 9/2014 | Sengun |
| 8,936,620 B2 | 1/2015 | Kaiser et al. |
| 9,370,350 B2 | 6/2016 | Norton |
| 9,445,803 B2 | 9/2016 | Marchand et al. |
| 9,451,938 B2 | 9/2016 | Overes et al. |
| 2002/0019635 A1 | 2/2002 | Wenstrom et al. |
| 2002/0188301 A1 | 12/2002 | Dallara et al. |
| 2003/0032961 A1 | 2/2003 | Pelo et al. |
| 2003/0176919 A1 | 9/2003 | Schmieding |
| 2003/0195565 A1 | 10/2003 | Bonutti |
| 2003/0220646 A1 | 11/2003 | Thelen et al. |
| 2003/0233098 A1 | 12/2003 | Markworth |
| 2004/0010264 A1 | 1/2004 | Acker et al. |
| 2004/0010287 A1 | 1/2004 | Bonutti |
| 2004/0030346 A1 | 2/2004 | Frey et al. |
| 2004/0073227 A1 | 4/2004 | Dreyfuss et al. |
| 2004/0073306 A1 | 4/2004 | Eichhorn et al. |
| 2004/0092933 A1 | 5/2004 | Shaolian et al. |
| 2004/0149093 A1 | 8/2004 | Tang |
| 2004/0193217 A1 | 9/2004 | Lubbers et al. |
| 2004/0260300 A1 | 12/2004 | Gorensek et al. |
| 2004/0267277 A1 | 12/2004 | Zannis et al. |
| 2005/0015153 A1 | 1/2005 | Goble et al. |
| 2005/0033362 A1 | 2/2005 | Grafton |
| 2005/0070906 A1 | 3/2005 | Clark et al. |
| 2005/0137600 A1 | 6/2005 | Jacobs et al. |
| 2005/0137601 A1 | 6/2005 | Assell et al. |
| 2005/0143741 A1 | 6/2005 | Timmermans et al. |
| 2005/0177168 A1 | 8/2005 | Brunnett et al. |
| 2005/0187537 A1 | 8/2005 | Loeb et al. |
| 2005/0203527 A1 | 9/2005 | Carrison et al. |
| 2005/0228399 A1 | 10/2005 | Kubo et al. |
| 2005/0251159 A1 | 11/2005 | Ewers et al. |
| 2005/0251208 A1 | 11/2005 | Elmer et al. |
| 2005/0283156 A1 | 12/2005 | Schmieding et al. |
| 2005/0288710 A1 | 12/2005 | Fallin et al. |
| 2006/0001518 A1 | 1/2006 | Hayashi et al. |
| 2006/0004369 A1 | 1/2006 | Patel et al. |
| 2006/0015108 A1 | 1/2006 | Bonutti |
| 2006/0074434 A1 | 4/2006 | Wenstrom et al. |
| 2006/0079904 A1 | 4/2006 | Thal |
| 2006/0100631 A1 | 5/2006 | Sullivan et al. |
| 2006/0155329 A1 | 7/2006 | Grafton et al. |
| 2006/0178748 A1 | 8/2006 | Dinger et al. |
| 2006/0189993 A1 | 8/2006 | Stone |
| 2006/0190042 A1 | 8/2006 | Stone et al. |
| 2006/0212055 A1 | 9/2006 | Karabey et al. |
| 2006/0247641 A1 | 11/2006 | Re et al. |
| 2006/0247642 A1 | 11/2006 | Stone et al. |
| 2006/0282085 A1 | 12/2006 | Stone et al. |
| 2006/0293689 A1 | 12/2006 | Miller et al. |
| 2007/0010843 A1 | 1/2007 | Green |
| 2007/0010857 A1 | 1/2007 | Sugimoto et al. |
| 2007/0032800 A1 | 2/2007 | Ortiz et al. |
| 2007/0093840 A1 | 4/2007 | Pacelli et al. |
| 2007/0191853 A1 | 8/2007 | Stone |
| 2007/0213734 A1 | 9/2007 | Bleich et al. |
| 2007/0213735 A1 | 9/2007 | Saadat et al. |
| 2007/0225721 A1 | 9/2007 | Thelen et al. |
| 2007/0233151 A1 | 10/2007 | Chudik |
| 2007/0255317 A1 | 11/2007 | Fanton et al. |
| 2007/0260259 A1 | 11/2007 | Fanton et al. |
| 2007/0276392 A1 | 11/2007 | Beyar et al. |
| 2007/0288023 A1 | 12/2007 | Pellegrino et al. |
| 2007/0288031 A1 | 12/2007 | Dreyfuss et al. |
| 2008/0004659 A1 | 1/2008 | Burkhart et al. |
| 2008/0009904 A1 | 1/2008 | Bourque et al. |
| 2008/0027446 A1 | 1/2008 | Stone et al. |
| 2008/0027457 A1 | 1/2008 | Dienst et al. |
| 2008/0046009 A1 | 2/2008 | Albertorio et al. |
| 2008/0058816 A1 | 3/2008 | Philippon et al. |
| 2008/0065080 A1 | 3/2008 | Assell et al. |
| 2008/0065092 A1 | 3/2008 | Assell et al. |
| 2008/0071282 A1 | 3/2008 | Assell et al. |
| 2008/0109037 A1 | 5/2008 | Steiner et al. |
| 2008/0114364 A1 | 5/2008 | Goldin et al. |
| 2008/0114399 A1 | 5/2008 | Bonutti |
| 2008/0132932 A1 | 6/2008 | Hoeppner et al. |
| 2008/0140078 A1 | 6/2008 | Nelson et al. |
| 2008/0140093 A1 | 6/2008 | Stone et al. |
| 2008/0140116 A1 | 6/2008 | Bonutti |
| 2008/0147063 A1 | 6/2008 | Cauldwell et al. |
| 2008/0147064 A1 | 6/2008 | Cauldwell et al. |
| 2008/0154275 A1 | 6/2008 | Assell et al. |
| 2008/0161814 A1 | 7/2008 | McAllister et al. |
| 2008/0167660 A1 | 7/2008 | Moreau et al. |
| 2008/0188854 A1 | 8/2008 | Moser |
| 2008/0188935 A1 | 8/2008 | Saylor et al. |
| 2008/0249481 A1 | 10/2008 | Crainich et al. |
| 2008/0255613 A1 | 10/2008 | Kaiser et al. |
| 2008/0262544 A1 | 10/2008 | Burkhart |
| 2008/0275431 A1 | 11/2008 | Stone et al. |

(56) References Cited

U.S. PATENT DOCUMENTS

| | | |
|---|---|---|
| 2008/0275453 A1 | 11/2008 | Lafosse et al. |
| 2008/0306483 A1 | 12/2008 | Iannarone |
| 2008/0312689 A1 | 12/2008 | Denham et al. |
| 2008/0319478 A1 | 12/2008 | Foerster et al. |
| 2009/0012526 A1 | 1/2009 | Fletcher |
| 2009/0018654 A1 | 1/2009 | Schmieding et al. |
| 2009/0024130 A1 | 1/2009 | Lombardo |
| 2009/0054928 A1 | 2/2009 | Denham et al. |
| 2009/0062854 A1 | 3/2009 | Kaiser et al. |
| 2009/0076514 A1 | 3/2009 | Haines |
| 2009/0082805 A1 | 3/2009 | Kaiser et al. |
| 2009/0099554 A1 | 4/2009 | Forster et al. |
| 2009/0105775 A1 | 4/2009 | Mitchell et al. |
| 2009/0131940 A1 | 5/2009 | Brunnett et al. |
| 2009/0138015 A1 | 5/2009 | Conner et al. |
| 2009/0138042 A1 | 5/2009 | Thal |
| 2009/0143784 A1 | 6/2009 | Petersen et al. |
| 2009/0149858 A1 | 6/2009 | Fanelli et al. |
| 2009/0157081 A1 | 6/2009 | Homan et al. |
| 2009/0160112 A1 | 6/2009 | Ostrovsky |
| 2009/0171359 A1 | 7/2009 | Sterrett |
| 2009/0192468 A1 | 7/2009 | Stone |
| 2009/0194446 A1 | 8/2009 | Miller et al. |
| 2009/0198258 A1 | 8/2009 | Workman |
| 2009/0216238 A1 | 8/2009 | Stark |
| 2009/0216243 A1 | 8/2009 | Re |
| 2009/0234386 A1 | 9/2009 | Dean et al. |
| 2009/0234451 A1 | 9/2009 | Manderson |
| 2009/0240104 A1 | 9/2009 | Ogdahl et al. |
| 2009/0248029 A1 | 10/2009 | Paulos |
| 2009/0265002 A1 | 10/2009 | Re et al. |
| 2009/0306671 A1 | 12/2009 | McCormack et al. |
| 2009/0306711 A1 | 12/2009 | Stone et al. |
| 2009/0312763 A1 | 12/2009 | McCormack et al. |
| 2009/0312776 A1 | 12/2009 | Kaiser et al. |
| 2009/0312792 A1 | 12/2009 | Fallin et al. |
| 2009/0312793 A1 | 12/2009 | Huxel et al. |
| 2009/0318961 A1 | 12/2009 | Stone et al. |
| 2009/0326538 A1 | 12/2009 | Sennett et al. |
| 2010/0049196 A1 | 2/2010 | Re |
| 2010/0049202 A1 | 2/2010 | Re |
| 2010/0057045 A1 | 3/2010 | Albritton, IV et al. |
| 2010/0076440 A1 | 3/2010 | Pamichev et al. |
| 2010/0082033 A1 | 4/2010 | Germain |
| 2010/0087857 A1 | 4/2010 | Stone et al. |
| 2010/0121332 A1 | 5/2010 | Crainich et al. |
| 2010/0121333 A1 | 5/2010 | Crainich et al. |
| 2010/0145384 A1 | 6/2010 | Stone et al. |
| 2010/0152739 A1 | 6/2010 | Sidebotham et al. |
| 2010/0160962 A1 | 6/2010 | Dreyfuss et al. |
| 2010/0185238 A1 | 7/2010 | Cauldwell et al. |
| 2010/0185283 A1 | 7/2010 | Baird et al. |
| 2010/0191241 A1 | 7/2010 | McCormack et al. |
| 2010/0211075 A1 | 8/2010 | Stone |
| 2010/0241121 A1 | 9/2010 | Logan et al. |
| 2010/0249786 A1 | 9/2010 | Schmieding et al. |
| 2010/0268275 A1 | 10/2010 | Stone et al. |
| 2010/0292732 A1* | 11/2010 | Hirotsuka ......... A61B 17/0401 606/232 |
| 2010/0292792 A1 | 11/2010 | Stone et al. |
| 2010/0305709 A1 | 12/2010 | Metzger et al. |
| 2011/0015674 A1 | 1/2011 | Howard et al. |
| 2011/0015675 A1 | 1/2011 | Howard et al. |
| 2011/0022083 A1 | 1/2011 | DiMatteo et al. |
| 2011/0022084 A1 | 1/2011 | Sengun et al. |
| 2011/0054526 A1 | 3/2011 | Stone et al. |
| 2011/0087247 A1 | 4/2011 | Fung et al. |
| 2011/0087280 A1 | 4/2011 | Albertorio |
| 2011/0087284 A1 | 4/2011 | Stone et al. |
| 2011/0098727 A1* | 4/2011 | Kaiser ............... A61B 17/0401 606/144 |
| 2011/0106089 A1 | 5/2011 | Brunnett et al. |
| 2011/0106153 A1 | 5/2011 | Stone et al. |
| 2011/0125189 A1 | 5/2011 | Stoll, Jr. et al. |
| 2011/0152927 A1 | 6/2011 | Deng et al. |
| 2011/0160767 A1 | 6/2011 | Stone et al. |
| 2011/0160768 A1 | 6/2011 | Stone et al. |
| 2011/0184516 A1 | 7/2011 | Baird et al. |
| 2011/0208194 A1 | 8/2011 | Steiner et al. |
| 2011/0208239 A1 | 8/2011 | Stone et al. |
| 2011/0208240 A1 | 8/2011 | Stone et al. |
| 2011/0213417 A1 | 9/2011 | Foerster et al. |
| 2011/0218538 A1 | 9/2011 | Sherman et al. |
| 2011/0218625 A1 | 9/2011 | Berelsman et al. |
| 2011/0224799 A1 | 9/2011 | Stone |
| 2011/0264140 A1 | 10/2011 | Lizardi et al. |
| 2011/0264141 A1 | 10/2011 | Denham et al. |
| 2011/0270278 A1 | 11/2011 | Overes et al. |
| 2011/0270293 A1 | 11/2011 | Malla et al. |
| 2011/0270306 A1 | 11/2011 | Denham et al. |
| 2011/0295279 A1 | 12/2011 | Stone et al. |
| 2011/0301708 A1 | 12/2011 | Stone et al. |
| 2011/0319896 A1 | 12/2011 | Papenfuss et al. |
| 2012/0004672 A1 | 1/2012 | Giap et al. |
| 2012/0041485 A1 | 2/2012 | Kaiser et al. |
| 2012/0041486 A1 | 2/2012 | Stone et al. |
| 2012/0046693 A1 | 2/2012 | Denham et al. |
| 2012/0053630 A1 | 3/2012 | Denham et al. |
| 2012/0053641 A1 | 3/2012 | Meridew |
| 2012/0059417 A1 | 3/2012 | Norton et al. |
| 2012/0059418 A1 | 3/2012 | Denham et al. |
| 2012/0071976 A1 | 3/2012 | May et al. |
| 2012/0089193 A1 | 4/2012 | Stone et al. |
| 2012/0095470 A1 | 4/2012 | Kaiser et al. |
| 2012/0095556 A1 | 4/2012 | Re et al. |
| 2012/0109142 A1 | 5/2012 | Dayan |
| 2012/0109156 A1 | 5/2012 | Overes et al. |
| 2012/0109194 A1 | 5/2012 | Miller et al. |
| 2012/0116452 A1 | 5/2012 | Stone et al. |
| 2012/0123474 A1 | 5/2012 | Zajac et al. |
| 2012/0130424 A1 | 5/2012 | Sengun et al. |
| 2012/0150203 A1 | 6/2012 | Brady et al. |
| 2012/0150297 A1 | 6/2012 | Denham et al. |
| 2012/0150301 A1 | 6/2012 | Gamache et al. |
| 2012/0165866 A1 | 6/2012 | Kaiser et al. |
| 2012/0165867 A1 | 6/2012 | Denham et al. |
| 2012/0165938 A1 | 6/2012 | Denham et al. |
| 2012/0172986 A1 | 7/2012 | Stone et al. |
| 2012/0179254 A1 | 7/2012 | Saliman |
| 2012/0180291 A1 | 7/2012 | Oren et al. |
| 2012/0197271 A1 | 8/2012 | Astorino et al. |
| 2012/0203231 A1 | 8/2012 | Long et al. |
| 2012/0203288 A1 | 8/2012 | Lange et al. |
| 2012/0209325 A1 | 8/2012 | Gagliano et al. |
| 2012/0239086 A1 | 9/2012 | Reznik et al. |
| 2012/0245585 A1 | 9/2012 | Kaiser et al. |
| 2012/0253355 A1 | 10/2012 | Murray et al. |
| 2012/0265205 A1 | 10/2012 | Steiner et al. |
| 2012/0290002 A1 | 11/2012 | Astorino |
| 2012/0290004 A1 | 11/2012 | Lombardo et al. |
| 2012/0290006 A1 | 11/2012 | Collins et al. |
| 2012/0296345 A1 | 11/2012 | Wack et al. |
| 2012/0296427 A1 | 11/2012 | Conner et al. |
| 2012/0303046 A1 | 11/2012 | Stone et al. |
| 2013/0012962 A1 | 1/2013 | Stone |
| 2013/0018416 A1 | 1/2013 | Lombardo et al. |
| 2013/0023928 A1 | 1/2013 | Dreyfuss |
| 2013/0023929 A1 | 1/2013 | Sullivan et al. |
| 2013/0023930 A1 | 1/2013 | Stone et al. |
| 2013/0035698 A1 | 2/2013 | Stone et al. |
| 2013/0046341 A1 | 2/2013 | Stone et al. |
| 2013/0053897 A1 | 2/2013 | Brown et al. |
| 2013/0072989 A1 | 3/2013 | Overes et al. |
| 2013/0085568 A1 | 4/2013 | Smith et al. |
| 2013/0096611 A1 | 4/2013 | Sullivan |
| 2013/0096612 A1 | 4/2013 | Zajac et al. |
| 2013/0110165 A1 | 5/2013 | Burkhart et al. |
| 2013/0131722 A1 | 5/2013 | Marchand et al. |
| 2013/0165972 A1 | 6/2013 | Sullivan |
| 2013/0178898 A1 | 7/2013 | Arnett et al. |
| 2013/0190819 A1 | 7/2013 | Norton |
| 2013/0237997 A1 | 9/2013 | Arai et al. |
| 2013/0245700 A1 | 9/2013 | Choinski |
| 2013/0268000 A1 | 10/2013 | Harner et al. |

(56) References Cited

U.S. PATENT DOCUMENTS

| | | | |
|---|---|---|---|
| 2013/0296893 A1* | 11/2013 | Dean | A61B 17/06166 606/145 |
| 2013/0296931 A1 | 11/2013 | Sengun | |
| 2013/0296934 A1* | 11/2013 | Sengun | A61B 17/0401 606/232 |
| 2013/0317544 A1 | 11/2013 | Ferguson et al. | |
| 2013/0325063 A1 | 12/2013 | Norton et al. | |
| 2013/0345749 A1 | 12/2013 | Sullivan et al. | |
| 2014/0039503 A1 | 2/2014 | Pilgeram | |
| 2014/0081322 A1 | 3/2014 | Sengun et al. | |
| 2014/0163679 A1 | 6/2014 | Re et al. | |
| 2014/0188163 A1 | 7/2014 | Sengun | |
| 2014/0257382 A1 | 9/2014 | McCartney | |

FOREIGN PATENT DOCUMENTS

| | | |
|---|---|---|
| DE | 4243715 A1 | 7/1994 |
| DE | 19503504 A1 | 3/1996 |
| EP | 153831 A2 | 9/1985 |
| EP | 253526 A1 | 1/1988 |
| EP | 0440371 A1 | 8/1991 |
| EP | 0611551 A1 | 8/1994 |
| EP | 1155776 A2 | 11/2001 |
| EP | 1369089 A2 | 12/2003 |
| EP | 2286742 A1 | 2/2011 |
| EP | 2544607 A1 | 1/2013 |
| EP | 2596755 A2 | 5/2013 |
| EP | 2662030 A1 | 11/2013 |
| EP | 2662032 A1 | 11/2013 |
| FR | 1166884 A | 11/1958 |
| FR | 2606996 A1 | 5/1988 |
| FR | 2676638 A1 | 11/1992 |
| GB | 2093353 A | 9/1982 |
| WO | 95011631 A1 | 5/1995 |
| WO | 00/44291 A1 | 8/2000 |
| WO | 0128457 A1 | 4/2001 |
| WO | 03007861 A1 | 1/2003 |
| WO | 2007/010389 A1 | 1/2007 |
| WO | 2008128075 A1 | 10/2008 |
| WO | 2009105880 A1 | 9/2009 |
| WO | 2011112371 A1 | 9/2011 |
| WO | 2012134999 A1 | 10/2012 |
| WO | 2012158583 A1 | 11/2012 |
| WO | 2013006820 A1 | 1/2013 |

OTHER PUBLICATIONS

Partial International Search Report for Application No. PCT/US2014/069087 dated Mar. 12, 2015.
Australian Examination Report for Application No. 2013202699 dated Feb. 21, 2014.
Extended European Search Report for Application No. EP14157877 dated Jul. 4, 2016.
BIOMET Sports Medicine: Micromax Flex Suture Anchor, (2008).
Burkinshaw, U.S. Appl. No. 60/418,545, filed Oct. 15, 2002.
Chen et al., Journal of Orthopaedic Research, pp. 1432-1438, Nov. 2009.
Chen et al., Poster No. 538, 54th Annual Meeting of the Orthopaedic Research Society, San Francisco, CA Mar. 2008.
Cole et al., American Journal of Sports Medicine, vol. XX, No. X, 2011.
CONMED: Linvatec: Shoulder Restoration System Y-Knot 1.3mm All Suture Anchor, © 2011 Linvatec Corporation, a subsidiary of ConMed Corporation—CBR 3057 (4 pages).
European Search Report, EP 10173568, dated Nov. 30, 2010.
Extended European Search Report for Application No. EP 12164104 dated Jul. 11, 2012.
HHS Tube, Fort Wayne Metals Research Products Corp., 2009.
International Search Report PCT/US2010/042264, dated Sep. 30, 2010.
Medtronic, The VISAO High-Speed Otologic Drill Catalog, 2007.
Perthes, German Surgery Periodical, vol. 85, Commermorative Publication, pp. 2-18, 1906.
Perthes, Ober Operationen bel habitueller Schulterluxaton, X, pp. 199-227, 85.
Sugaya et al., Journal of Bone and Joint Surgery, vol. 85-A, No. 5, pp. 878-884, May 2003.
U.S. Appl. No. 13/085,882, filed Apr. 13, 2011.
U.S. Appl. No. 13/303,849, filed Nov. 23, 2011.
U.S. Appl. No. 13/368,730, filed Feb. 8, 2012.
U.S. Appl. No. 13/588,586, filed Aug. 17, 2012.
U.S. Appl. No. 13/588,592, filed Aug. 17, 2012.
U.S. Appl. No. 13/783,804, filed Mar. 4, 2013.
U.S. Appl. No. 13/792,982, filed Mar. 11, 2013.
U.S. Appl. No. 61/679,336, filed Aug. 3, 2012.
Extended European Search Report for Application No. EP14157129 dated Oct. 9, 2014.

* cited by examiner

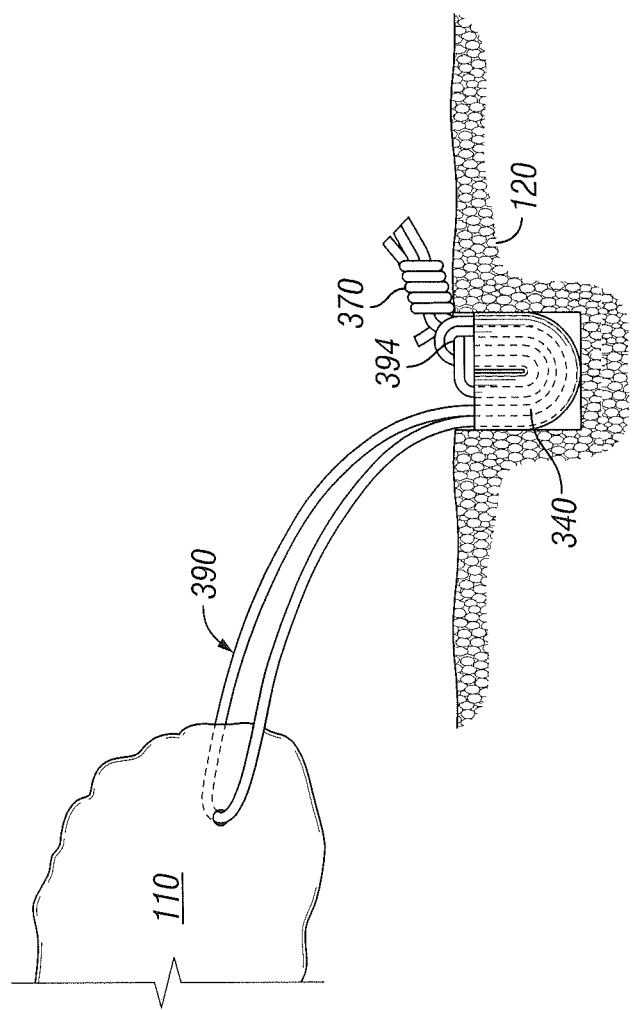

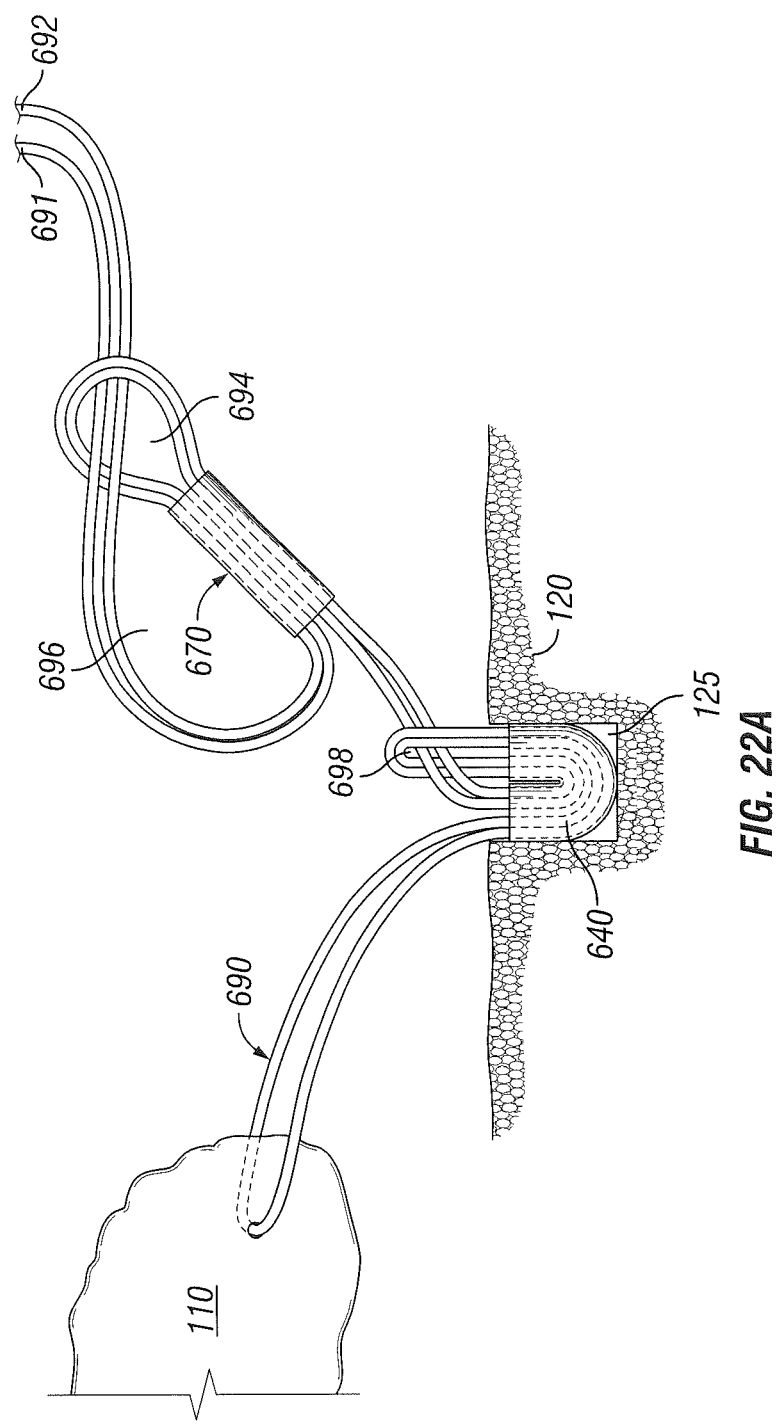

FILAMENT ENGAGEMENT SYSTEM AND METHODS OF USE

BACKGROUND OF THE INVENTION

Soft tissue structures, such a ligaments and tendons, connect multiple anatomic components together. Whether the connection is bone-to-bone, muscle-to-bone, or some other linkage, these soft tissue structures are often, if not permanently, subject to tension forces. Injuries can partially or completely sever such structures leading to immobility and/or dysfunction of the anatomic components. In one example, a shoulder injury may tear a portion of the rotator cuff from its connection to bone, leading to instability of the shoulder joint and causing the naturally tensioned tendon to slacken.

In some instances surgery may be needed to repair or replace the damaged soft tissue structure, which often involves pulling the native soft tissue or a soft tissue graft into a natural state of tension and into a position for healing. Maintaining the soft tissue in a healing position and in a constant and consistent state of tension may be beneficial in allowing the soft tissue to heal as closely to a natural state as possible and to prevent any healing progress from becoming undone.

Generally, an anchoring support and, optionally, a filament attached to the anchoring support are utilized in soft tissue reparation. A recent trend in tissue anchor and suture anchor devices is the "soft" device, also referred to as a "filamentary" fixation device, in which the device itself is constructed of a filamentary material, such as suture or the like. Such filamentary fixation devices can replace traditional metal or hard polymer devices in numerous soft tissue repair and replacement surgical procedures. Such filamentary fixation devices may provide solutions to various problems encountered with traditional metal or hard polymer devices. In many instances, such traditional devices tend to be large in diameter, and must include sufficient material, or other additional structures, to withstand the forces pulling against the device, whether via a suture or directly against the device itself. The size of such devices may limit the possible implantation locations in the body, as sufficient bone mass is required to accommodate the device. Moreover, a large hole must be drilled into the bone to allow for passage of the device through the cortical layer and into the cancellous bone. The larger drill holes may be too invasive resulting in excessive loss of healthy bone, or creation of a large repair site.

Despite the many benefits these filamentary fixation devices provide, such devices can benefit from alternative filament securement techniques as securing the filament is often the major difficulty faced when using such filamentary fixation devices.

BRIEF SUMMARY OF THE INVENTION

Generally, disclosed herein are devices, assemblies, systems, kits and methods of using the same in particular regard to knotless filament anchoring applications. In one aspect, a system for securing a length of filament in working communication with tissue. The system includes a first filamentary sleeve having a length along a longitudinal axis and a passageway therethrough. The passageway is dimensioned to allow slidable movement therein of a length of filament. Also included within the system is a filament engagement device that includes a pathway. The pathway has a first configuration and a second configuration, wherein a portion of the length of filament is slidable within the pathway when the pathway is in the first configuration and is restricted from sliding when the pathway is in the second configuration.

Additionally, the first filamentary sleeve may be adapted to be positioned in a tissue and deployed therein to become fixedly secured to the tissue. Also, the filament engagement device may be a second filamentary sleeve formed of filament or deformable polymer. The filament engagement device may be at least one of deformable or compressible upon application of force by the filament. Further, the second sleeve may include a first and second end and a distance therebetween. The distance may be larger when the pathway is in the first configuration than in the second configuration.

Continuing with this aspect, the engagement device may be a sliding knot formed from filamentary material, and said sliding knot may be a nail knot. The pathway may be defined by the loops of the nail knot. In the first configuration, the loops of the nail knot may each have a diameter dimensioned to allow for slidable movement of the length of filament therein, and in the second configuration, the loops of the nail knot may each have a diameter dimensioned to inhibit slidable movement of the length of filament therein.

The system may also include a filamentary shuttle that has a first end adapted to receive and retain at least a portion of the length of filament. The filamentary shuttle may also include a first diameter equal to or larger than a diameter of the length of filament. Additionally, the passageway of the first filamentary sleeve may be dimensioned to allow slidable movement therein of the filamentary shuttle when the first filamentary sleeve is curved along its length. At least a portion of the filamentary shuttle may be positioned within the passageway of the first filamentary sleeve and within the pathway of the filament engagement device. Alternatively, at least a portion of the filamentary shuttle may be positioned within one of the passageway of the filamentary sleeve or the pathway of the filament engagement device. The first end of the filamentary shuttle may include an eyelet or a hook and may be constructed of metal wire or filament.

In another aspect of the present invention, a method for securing a length of filament having two free ends in working communication with tissue. The method includes the step of passing at least one free end of the length of filament through a passageway of a first sleeve. Another step of the method includes obtaining a second sleeve that includes a length along a longitudinal axis, a first end and a second end, and a pathway that extends between the first end and second end. Also included in the method is the step of passing at least a portion of the length of filament through the pathway of the second filamentary sleeve such that at least one free end extends from the first end and a loop configuration formed by a portion of the length of the filament extends from the second end. Additionally, the method includes the step of passing the at least one free end of the length of filament through the loop configuration. Further included in the method is the step of tensioning the at least one free end such that the loop configuration travels towards and at least partially into the second sleeve. The length of the filament is adapted to apply tension to the tissue, and the at least one filament free end, passed through the loop configuration, is secured within the loop configuration.

Further, the first sleeve may be made from filamentary material, and the method may also include the steps of implanting the first sleeve into a prepared bore hole in a bone and deploying the first sleeve such that the first sleeve is fixedly secured within the bore hole. Another step that may be included in method is the step of sliding the second sleeve along the length of filament towards the first filamentary sleeve such that at least a portion of the second sleeve is positioned within or over the bore hole. The second sleeve may be made from one of a filamentary material or a deformable polymer.

Continuing with this aspect, the step of tensioning may include compressing the second sleeve such that the first end moves closer to the second end. Further, the step of passing at least a portion of the length of filament through the pathway of the second sleeve may include: passing at least a portion of the length of filament into the second sleeve through the first end, and continuing to pull at least a portion of the length of filament through the second sleeve and out the second end, thereby forming the loop configuration on the length of filament outside the second end. In this position, the length of filament may be folded over itself, forming the loop configuration at the second end and the at least one free end at the first end.

Additionally, the step of passing at least a portion of the length of filament through the pathway of the second filamentary sleeve may include: pulling the at least one free end of the length of filament through the first end into the pathway and out the second end of the second filamentary sleeve, and pulling the at least one free end of the length of filament through the second end into the pathway and out the first end such that a portion of the length of filament extends from the second end thereby forming the loop configuration. The steps of pulling may be performed with a filament shuttle.

In a further aspect, a method for securing a length of filament in working communication with both tissue and a tissue anchor and having two free ends. The method includes the step of obtaining a first sleeve having a length along a longitudinal axis, a first end and second end, and a passageway extending through the first end and second end. The method also includes the step of pulling at least a portion of the length of filament into the first end and through the passageway such that at least one free end extends from the first end and a loop configuration extends from the second end. Additionally, the method includes the steps of passing the at least one free end through the loop configuration, and tensioning the at least one free end to compress the first sleeve.

Additionally, the first sleeve may be made from one of a filamentary material or a deformable polymer. Further, the method may include the step of sliding the first sleeve toward a prepared bore hole in a bone to a position within or adjacent the bore hole. Also, the obtaining step may include a second sleeve, and prior to the pulling step, the method may include implanting the second sleeve into the bore hole and deploying the second sleeve to fixedly secure the second sleeve therein.

In yet another aspect, a method for securing a length of filament in working communication with tissue and having two free ends. The method includes the step of obtaining a first sleeve. The first sleeve includes a length along a longitudinal axis, a first and second end, and a passageway extending through the first and second end. The method also includes pulling at least a portion of the length of filament into the first end and through the passageway such that at least one free end extends from the first end and a loop configuration extends from the second end of the first sleeve. The method also includes the steps of passing the first free end through the loop configuration and forming a sliding knot on the length of filament between the at least one free end and loop configuration. Additionally, the method includes cinching or tightening the sliding knot against the length of filament.

Also, the first sleeve may be made from one of a filamentary material or a deformable polymer. Additionally, the method may include the step of sliding the sliding knot toward a prepared bore hole in a bone to a position within or adjacent the bore hole. The sliding knot may be a nail knot.

BRIEF DESCRIPTION OF THE DRAWINGS

These and other features, aspects, and advantages of the present invention will become better understood with regard to the following description, appended claims, and accompanying drawings where:

FIG. 20 illustrates another step of the method embodiment of FIGS. 15-19.

FIGS. 22A and 22B illustrate another alternative method of use.

DETAILED DESCRIPTION

The fixation devices, assemblies, systems, kits and associated methods of use of the present invention are intended for use in the repair, reattachment, replacement or otherwise securement of tissue, including both hard tissue (i.e., bone or the like) and soft tissue. Soft tissue may be, for example, meniscus, cartilage, capsule, ligaments and tendons, replacement grafts of any of these soft tissues, or the like.

While many of the exemplary methods disclosed herein are directed towards the use of filamentary fixation assemblies and systems involving a filament/suture anchor for implantation into a bone hole, other uses, some of which are described herein, are also envisioned. Additionally, the devices, assemblies, kits and methods disclosed herein are contemplated for use in both open surgery and arthroscopic surgery. As used herein, "proximal" or "proximally" means closer to or towards an operator, e.g., surgeon, while "distal" or "distally" means further from or away from the operator.

As used herein, the term "filament" or "filamentary" is defined as a suture or other thread-like material. Such filaments may be constructed of synthetic material (e.g., PLGA, UHMWPE (ultra high molecular weight polyethylene), polyester, PEEK, Nylon, polypropylene, aramids (for example Kevlar®-based fibers) or the like, or blends thereof), organic material (silk, animal tendon, or the like or blends thereof), or blends of both one or more organic materials and one or more synthetic materials. Alternatively, filaments may include thin metal wires. While any of these materials may be used, it is preferable, and is disclosed herein, that the various filaments or filamentary aspects of the present invention be constructed out of suture, such as UHMWPE, polyester or blends thereof.

Figure 1:
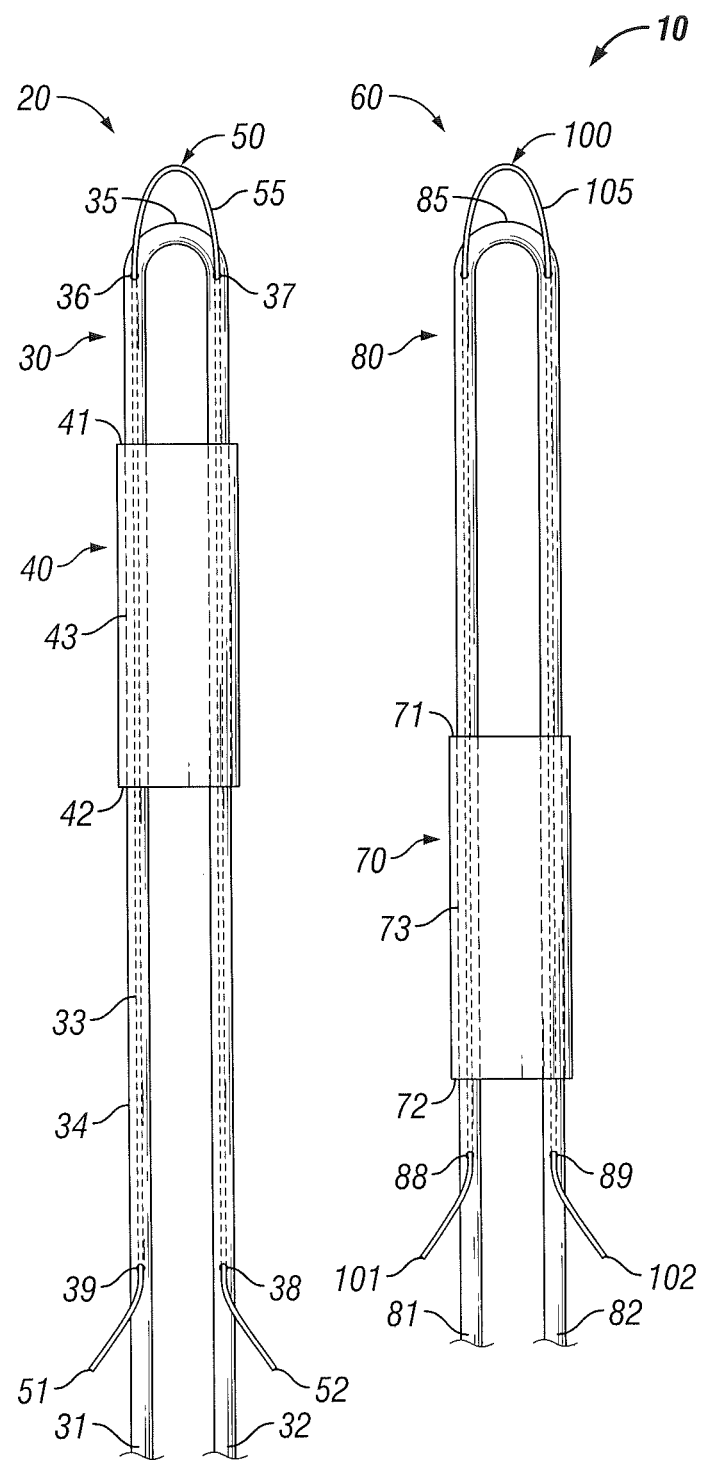
FIG. 1 illustrates an embodiment of a filamentary fixation system including a first and second filamentary fixation assembly.

In one embodiment of the present invention, as illustrated in FIG. 1, a filamentary fixation system 10, includes a first filamentary fixation assembly 20, and a second filamentary fixation assembly 60. The first filamentary fixation assembly 20 generally includes a first filamentary sleeve 40 and a first filamentary shuttle 30. The second filamentary fixation assembly 60 generally includes a second filamentary sleeve 70 and a second filamentary shuttle 80.

The first filamentary sleeve 40 includes a generally cylindrical shape along a longitudinal axis defined by a first end 41 and a second end 42, and a hollow passageway 43 extending therethrough along the longitudinal axis. While this first filamentary sleeve 40 is one embodiment, it is envisioned that alternative configurations of the sleeve may also be incorporated into the various assemblies, shapes, sizes, or features as desired. Various examples of which are disclosed in U.S. application Ser. No. 13/783,804, filed Mar. 4, 2013, the entirety of which is incorporated by reference herein as is fully set forth herein and which is assigned to the same entity as the present application. Additional examples of alternative configurations are disclosed in U.S. Provisional Application No. 61/679,336, filed Aug. 3, 2012; U.S. application Ser. No. 13/303,849, filed Nov. 23, 2011; Ser. No. 13/588,586, filed Aug. 17, 2012; Ser. No. 13/588,592, filed Aug. 17, 2012; and U.S. Pat. Nos. 5,989,252 and 6,511,498, the entireties of which are incorporated by reference herein as is fully set forth herein and all of which are assigned to the same entity as the present application. Another exemplary first filamentary sleeve for use in the present invention is the Iconix® line of filamentary fixation products (Stryker Corporation, Kalamazoo, Mich.). Other alternative configurations are also envisioned.

Figure 2A:
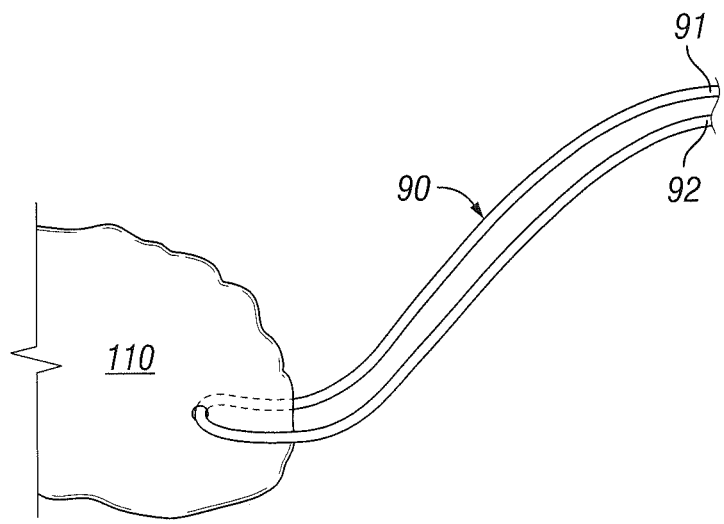
FIG. 2A illustrates a step of one embodiment of the use of the filamentary fixation system of FIG. 1.
Figure 2B:
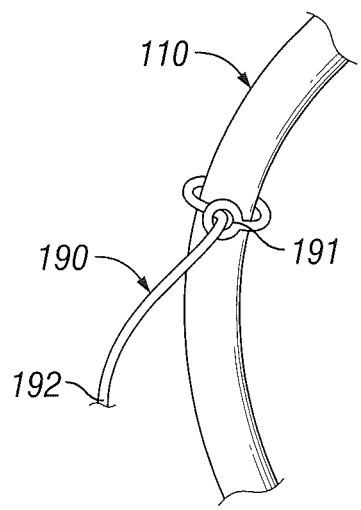
FIGS. 2B-2C illustrates alternative steps of the use of the filamentary fixation system of FIG. 1.
Figure 2C:
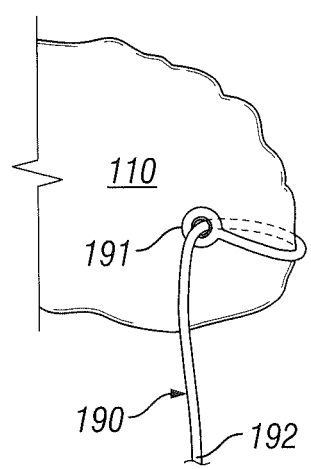

The first filamentary shuttle 30 may be formed in any manner capable of capturing a filament, such as the length of repair filament 90 depicted in FIGS. 2A-2C, and passing it through the passageway 43 of sleeve 40. Illustrated in FIG. 1 is one embodiment of shuttle 30 which includes a first end or tail 31 and a second end or tail 32, a length therebetween, and an interior passageway 33 along at least a portion of the length. The shuttle 30 may also include at least two openings 36, 37, and optionally at least four openings 36, 37, 38, 39 (as in FIG. 1), which extend through a sidewall from the interior passageway 33 to an outer surface 34 of the shuttle.

As the shuttle 30 is preferably constructed from a length of suture having a hollow core, the interior passageway 33 would extend along the entire length of the shuttle filament 30. However, if the shuttle is constructed of another material, or is formed from a unique braid, weave pattern, or the like, the passageway may not extend the entire length of the shuttle, though it should at least extend along the length of the shuttle spanning the distance between the at least two openings, or at least four openings, if four openings are present (as illustrated in FIG. 1), for reasons discussed further below. Shuttle 30 can also include a structure for engaging the length of filament 90 (described in detail below), such as a loop structure as exemplified by loop configuration 35. While one embodiment of shuttle 30, 80 is illustrated, any shape or configuration capable of passing suture through hollow passageway 43 and/or pathway 73.

Additionally, an optional inner filament 50 can be positioned within at least a portion of the interior passageway 33 of the filamentary shuttle 30. As illustrated in FIG. 1, for example, the inner filament 50 can extend through the passageway 33, from end 31 and towards the loop configuration 35, and out of opening 36. The inner filament 50 can continue outside of the passageway 33 toward opening 37, forming a structure for engaging the length of filament 90 (described in detail below) outside of the passageway 33 and at a position on or adjacent to the loop configuration 35. The inner filament 50 can then pass through opening 37 and back into passageway 33, towards end 32. This engaging structure can be a loop structure as is exemplified by filament eyelet 55. The inner filament 50 first and second ends 51, 52 may remain in position within the inner passageway 33, may extend to and through the first and second ends 31, 32 of the shuttle 30, or, as illustrated, exit the passageway 33 through additional openings 38, 39.

The first filamentary shuttle 30, with or without the inner filament 50 present, in turn, can be folded over itself, as in FIG. 1, forming the loop configuration 35, with the first and second ends 31, 32 extending therefrom. In this position, the shuttle 30 can be positioned through the hollow passageway 43 of the first filamentary sleeve 40 such that at least a portion of the loop configuration 35 is positioned outside the passageway 43 at the first end 41 of the first filamentary sleeve 40, and the first and second ends 31, 32 extend through the passageway 43 and out past the second end 42 of the first filamentary sleeve 40. The first filamentary shuttle 30 may be positioned as such, for example, by the use of a separate length of wire or suture (not shown) positioned through the passageway 43 and having a loop or hook on one end (and further, such length of wire or suture could in fact be alternative embodiments of shuttle 30). The first filamentary shuttle 30 may be engaged with the loop or hook and pulled into and through the sleeve 40 to a position as illustrated in FIG. 1. One example of such use of a loading wire or suture is illustrated in the heretofore referenced '586 and '592 applications, incorporated by reference herein.

While the first fixation assembly 20 illustrated in FIG. 1 depicts the first filamentary shuttle 30 being folded along its length and including an inner filament 50, various other filamentary shuttles are contemplated for use in conjunction with the first filamentary sleeve 40. Examples of alternative filamentary shuttles are described in the heretofore referenced applications, such as the '804 application incorporated by reference herein.

It is preferred, as illustrated in FIG. 1 and throughout this disclosure, that the first filamentary sleeve be constructed of a filament which has a larger inner diameter than an outer diameter of the first filamentary shuttle 30, and that the shuttle 30 has a larger outer diameter than either of the inner filament 50 and the length of filament 90. Moreover, the inner diameter of the passageway 33 of the first filamentary shuttle 30 should be equal to or greater than the outer diameter of the inner filament 50. Additionally, the inner diameter of the hollow passageway 43 of the sleeve 40 should be equal or greater than the outer diameter of filament 90, which may allow for simplified maneuvering of the filament 90, relative to the first filamentary sleeve 40, during manipulation in the various methods described below. However, such sizes may be dependent upon the desires of the operator and whether a tighter or looser fit is desired between the various filamentary elements of the present invention. In one example, the first filamentary shuttle 30 may be #5 suture, the inner filament 50, if present, may be #1 suture, and the length of repair filament 90 may be #2 suture (which is normally used for working or repair suture in the orthopedic field).

The second filamentary sleeve 70 is similar to the first filamentary sleeve 40, but may include various differences. The second filamentary sleeve 70 may similarly have a generally cylindrical shape along a longitudinal axis that is defined by a first end 71, a second end 72, and a hollow pathway extending therethrough 73. In some embodiments, the second filamentary sleeve 70 may be identical to the first filamentary sleeve 40. In other embodiments, the second filamentary sleeve 70 may vary in length, shape, diameter, and/or overall construction in relation to the first filamentary sleeve 40. For example, the second filamentary sleeve 70 may be shorter or longer than the first filamentary sleeve 40 and may be constructed from filamentary material that is more flexible than the material constituting the first filamentary sleeve 40. In another example, the second filamentary sleeve 70 may have a weave pattern that provides added strength and resilience to wear and tearing at the first and second ends 71, 72 of the second filamentary sleeve 70, while the first filamentary sleeve 40 may not have such a weave pattern or may have a weave pattern that provides different characteristics such as added strength and resilience to wear and tearing along its length. In further examples, the second filamentary sleeve 70 may be constructed from a material and/or may have a weave pattern or shape that allows for the second filamentary sleeve 70 to be compressed between the first and second ends 71, 72 into a more compact state longitudinally than that of the first filamentary sleeve 40 under similar loads. In yet another example, the second filamentary sleeve 70 may have an ovular cross-sectional geometry or an elliptical or hourglass shape between the first and second ends 71, 72, while the first filamentary sleeve may remain cylindrical.

As illustrated in FIG. 1, the second filamentary shuttle 80 may be identical to the first filamentary shuttle 30. In such an embodiment, the filament eyelet 105, if present, may be utilized to ensnare the length of filament 90 and may be constructed from filamentary material such that the filament eyelet 105 can be easily cut with common surgical instruments to facilitate the release of the ensnared length of filament 90. Alternatively, the length of filament 90 may be released by separating the inner filament 100 from the remainder of the filamentary shuttle 80 as described further below. Alternatively, if filament 100 is not present, the filament 90 may simply be ensnared by shuttle 80, for instance, by loop configuration 85.

In other embodiments, both the first and second filamentary sleeve 40, 70 may utilize only one filamentary shuttle. In such an embodiment, the filamentary shuttle may be longer than the first and second filamentary shuttles 30, and pass through and engage both first and second filamentary sleeves 40, 70 simultaneously, such that sleeves 40 and 70 are in a stacked configuration along the length of the shuttle.

In some embodiments, the second filamentary shuttle 80 may include a closed-loop at one end that generally limits release of the length of filament 90 to sliding the first and/or second end 91, 92 of the length of filament 90 back through the loop. However, alternative mechanisms of release may be possible where the material is capable of being easily cut during a surgical procedure. In one example, the second filamentary shuttle may not be constructed from filamentary material, but rather may be constructed from flexible metallic material such as a memory metal, such as a Nickel-Titanium alloy, also known as Nitinol, an example of which can be seen in FIGS. 7 and 8 of the present disclosure and can also be found in U.S. Provisional Application No. 61/755,654, filed Jan. 1, 2013 the entirety of which is hereby incorporated by reference herein as if fully set forth herein and is assigned to the same entity as the present application. In such an embodiment, the shuttle may have an elongate shaft 202 and a head 204 at one end of the shaft 202 forming a compressible closed loop 206 that may be rounded or diamond shaped for ensnaring the length of filament 90. The closed loop 206 may have an expanded state where the loop 206 provides a large enough opening to facilitate ensnarement of the length of filament 90 and a compressed state to facilitate movement through the second filamentary sleeve 70 as well as facilitate grasping of the length of filament 90.

In another closed-loop embodiment (not shown), the second filamentary shuttle may be made of filamentary material and have a lasso-type closed loop that can be expanded and retracted in order to capture and retain the length of filament 90 and also allow for the length of filament 90 to be released by cutting the loop or deconstructing the loop. The lasso-type embodiment may have various forms. For example, a single length of filamentary material may have a sliding knot or be spliced along its length to form a loop at one end of the material and a free end at the other end of the material. A semi-rigid sleeve may extend between the loop and the free end, wherein tensioning the free end of the filamentary material may slide a portion of the material through the semi-rigid sleeve to reduce the size of the loop.

In another embodiment, the second shuttle may have an open loop or hook-like configuration for ensnaring the length of filament 90 and allowing for release without the need to pass the free ends 91, 92 of the length of filament 90 back through the loop. In one example, a crochet hook, such as the crochet hook provided in the line of Champion® shoulder instrumentation (Howmedica Osteonics, Mahwah, N.J.), may be utilized by inserting the crochet hook through the pathway 73 of the second filamentary sleeve 70 so that the length of filament 90 can be retrieved within the joint and passed through the second filamentary sleeve 70.

In yet another embodiment, the second shuttle may be constructed to include a retrieving loop or filamentary grasping mechanism that can be selectively closed or opened via the actuation of an actuation member. An example of such an embodiment is a suture grasper that includes independently movable arms that are actuated by scissor-like finger loops, such as the suture grasper provided in the Champion® line of shoulder instrumentation.

FIG. 2A-2C illustrate the length of repair filament 90 having first and second free ends 91, 92. As discussed in detail below, the length of repair filament 90 and/or plurality of repair filaments 90 are used to engage the soft tissue, or otherwise apply tension or force to soft tissue, and secure tissue by similarly engaging the first filamentary sleeve 40 and second filamentary sleeve 70 in a manner which does not require any knots. Such repair filament 90 may be provided in standard lengths to be utilized within system 10.

A further embodiment of the present invention is a kit that includes at least one first filamentary fixation assembly 20, at least one second filamentary fixation assembly 60, and a plurality of lengths of filament 90. The plurality of filaments 90 can vary in length, color, diameter, strength, or the like, or they can be identical to one another. In one example, such a kit may be packaged and offered to operators as a kit for labrum repair in which a plurality of filaments may be used with a single first and second fixation assembly 20, 60 (packaged as a unit (as in FIG. 1), or separately).

In another example, the kit may include a single filamentary shuttle 30 engaged with and passing through both first and second filamentary sleeves 40, 70. In yet another example, such a kit may include a first fixation assembly 20, a plurality of filaments 90, and a second filamentary sleeve 70 packaged as a unit and a filamentary shuttle or other type of shuttle for use in conjunction with the second filamentary sleeve 70 packaged separately.

Such kits can also include additional components, such as at least one insertion instruments, for example the insertion instrument disclosed in the heretofore referenced '804 application, for inserting the first filamentary sleeve 40 into a bore hole in bone. Other instrumentation that may be included in such kits include a cannula, a drill or reamer (not shown) for preparation of the bore hole in bone (if required), needles (particularly for meniscus repair) and/or trocars which may be used to position the length of filament 90 around or through tissue (or, for example, through meniscus tissue and a tear through the meniscus tissue), and a loading wire or suture as discussed above for positioning each shuttle 30, 80 within their respective sleeves 40, 70 (though, it is preferred that each shuttle 30, 80 be positioned within their respective sleeve 40, 70 at time of manufacture, and thus would arrive at the operator packaged as such). Additional instrumentation that can be provided include knot pushers, or the like, to facilitate sliding and tightening of a one-way sliding cleat, or sliding knot, such as a nail knot, as described below, particularly through an arthroscopic cannula.

While the disclosed filamentary fixation devices, assemblies, systems and kits are preferred, it is also envisioned that other fixation devices, other than filamentary fixation devices 40 and 70, can also be used in any of the devices, systems, kits and assemblies and methods of use and assembly described or envisioned herein. For example, a tubular, flexible, plastic implant can replace the first filamentary sleeve 40. Alternatively, traditional suture anchors could also be used in lieu of first filamentary sleeve 40. In another example, filamentary sleeve 70 can be a rigid yet flexible cylindrical device (not shown). Such a device may be cylindrical and have a pathway extending through a first and second end and be made from a material such as PEEK or Nitinol.

Certain exemplary embodiments of methods of use will now be described. While such methods are described in terms of repair and reattachment of labrum tissue to a glenoid, it is envisioned that the systems and assemblies of the present invention may be performed in other anatomical locations and for other anatomical repairs such as, for example, acetabular labral repair, meniscal repair, rotator cuff repair, and the like. Similarly, it is envisioned that the filamentary fixation devices, assemblies, and systems of the present invention may also be used in bone-to-bone repair such as reducing fractures, reattaching bone fragments and chips to bone, and for the repair of bone-to-bone joints such as the acromioclavicular joint. However, for ease of reference, the methods of assembly and use will be directed towards the repair of soft tissue using the filamentary fixation system 10, and specifically, the deployment of the first filamentary sleeve 40 into a bore-hole in the glenoid for repair and reattachment of labrum tissue, unless stated otherwise.

FIGS. 2-13 are simplified illustrations of an embodiment of a method of use. As previously mentioned, the disclosed devices, assemblies, and systems can be used and the disclosed methods can be performed in conjunction with an open surgical procedure or arthroscopic surgical procedure. It should be understood that these figures are presented in such a way merely for the sake of clarity and that each of the illustrated steps can be and are preferably performed through a cannula.

To begin, an incision or plurality of incisions are generally made to gain access to the damaged tissue 110, such as the labrum, and the desired segment of bone 120, such as the glenoid, to be utilized for anchoring the tissue 110. As previously mentioned, working access to the tissue 110 and bone 120 may be and is preferably through an arthroscopic cannula or a plurality of arthroscopic cannulas. Thereafter, a bone drill may drill a bore hole 125 into the designated segment of bone 120. In some embodiments the bore hole 120 may be a blind hole that has a uniform diameter, and in other embodiments, the bore hole may be an undercut hole where the diameter of the bore hole varies along the length of said hole.

As illustrated in FIG. 2A, the single length of filament 90 may be passed through the tissue 110, for example via a suture passer, such that the first and second ends 91, 92 extend from tissue 110 in opposite directions. If desired, the filament 90 could be passed through tissue 110 more than once, for example, passed twice to create what is commonly called a mattress stitch.

In an alternative embodiment as illustrated in FIGS. 2B and 2C, a length of filament 190 may include a loop 191 and one free end 192. The loop 191 may be used in such a way that the filament 190 may be passed through or around tissue 110 as illustrated in FIGS. 2B and 2C, respectively, and free end 192 may be passed through the loop 191 and tensioned to draw the loop 191 against the tissue in a "luggage tag" configuration. Of course, in this instance, the filament 190 would only have one free end, that is free end 192, extending from the tissue 110 rather than two ends, such as ends 91 and 92 as when the filament 90 is used. However, a filament that includes two lengths of filament extending from the loop 191 may also be used to provide the operator with two free ends even when a luggage tag arrangement is used. Examples of such filaments are disclosed in U.S. application Ser. No. 13/441,290, filed Apr. 6, 2012, the entirety of which is incorporated by reference herein as if fully set forth herein, and which is assigned to the same entity as the present application. In another embodiment (not shown), an alternative "luggage tag" configuration can be formed by folding the length of filament 90 along its length to form a loop and two ends 91 and 92. The loop is passed through or around tissue 110, and free ends 91 and 92 are then passed through the loop to form a "luggage tag" configuration that includes two free ends 91, 92.

Regardless of which embodiment of the length of filament is utilized (and continuing as to the length of filament 90 for discussion purposes), once the length of filament 90 has sufficiently engaged the tissue 110, whether passing through the tissue 110 or looped around the tissue 110, the free ends 91, 92 are retrieved and brought outside the surgical site. Alternatively, the free ends 91, 92 may remain within the surgical site for the performance of the below described steps of this method, which can be performed with the assistance of an arthroscope or other viewing instrumentation known in the art.

Figure 3:
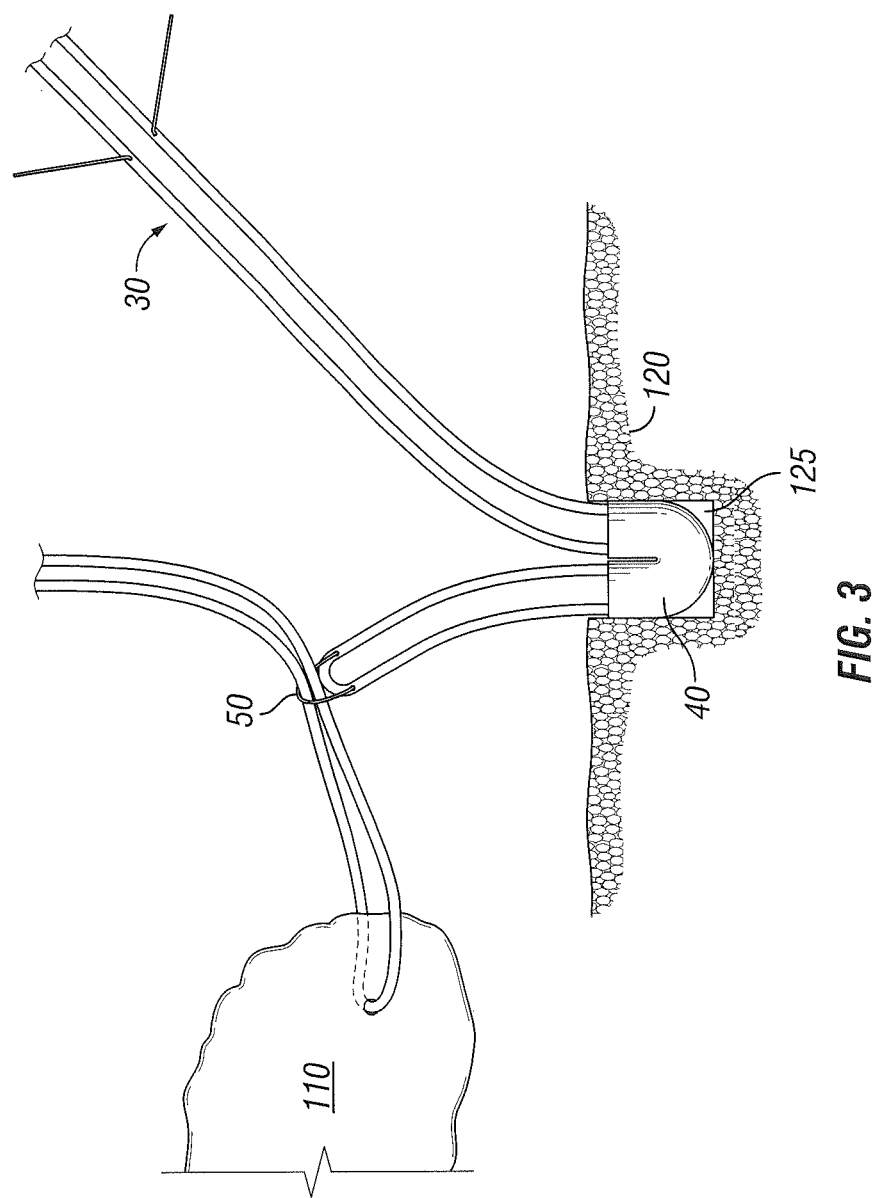
FIG. 3 illustrates another step of the method embodiment of FIG. 2.

FIG. 3 illustrates the next steps of engaging the length of filament 90 with the loop configuration 50 and positioning and deploying the first filamentary sleeve 40 within the bore hole 125. With the first and second ends 91, 92 of the length of filament 90 extending from tissue 110 and from the surgical site, first filamentary sleeve 40 may be positioned within the bore hole 125 and deployed, or, optionally, the first and second ends 91, 92 may be threaded through the loop configuration 50 prior to positioning within the bore hole 125. The first filamentary sleeve 40 assembled with the first filamentary shuttle 30 may be folded over the distal end of an insertion instrument (not shown), which has a distal end capable of retaining and inserting the first filamentary sleeve into the bore hole 125. Such an instrument and its use for implanting the first filamentary sleeve 125 is described in detail in the heretofore referenced '804 application. Generally, first filamentary shuttle 30 is sufficiently long such that both the loop configuration 35 and the first and second ends 31, 32 can extend proximally toward the operator and can be held and/or controlled by the operator as the insertion instrument is utilized to position the first filamentary sleeve 40 into the bore hole 125. The distal end of the insertion instrument is then guided into the bore hole 125 where the first filamentary sleeve 40 is ready for deployment.

Such deployment is achieved by the operator grasping and tensioning, in a proximal direction, the first and second ends 31, 32 and the loop configuration 35. Such deployment of the first filamentary sleeve 40 renders the sleeve 40 fixedly secured within the bore hole 125 such that the first filamentary shuttle 30 may be used to pass the length of filament 90 therethrough while the sleeve 40 remains within the bore hole 125. Of course, such deployment may alternatively be only a partial deployment wherein the sleeve 40 partially deploys, and as such, the sleeve 40 is removeably secured within the bore hole 125. However, from a practical standpoint, it is preferred that the operator fully deploy the first filamentary sleeve 40 such that, during the tensioning step of the filament 90 and tissue 110, the sleeve 40 does not inadvertently exit the bore hole 125, though it is appreciated that the tensioning of the filament 90 and tissue 110 may result in additional deployment (e.g., crushing or bunching of the first filamentary sleeve 40, or possible movement of the sleeve 40 relative to the surrounding bone 120). Such deployment is discussed further in the heretofore referenced applications incorporated by reference herein.

With the first filamentary sleeve 40 in the bore hole 125, and deployed towards or into an anchoring configuration, the sleeve 40 is now ready for engagement with the length of filament 90. The first and second ends 91, 92 of the length of filament 90 may be threaded through the filament eyelet 55 of the first filamentary shuttle 30, if not already done so, as illustrated by FIG. 3.

Figure 4:
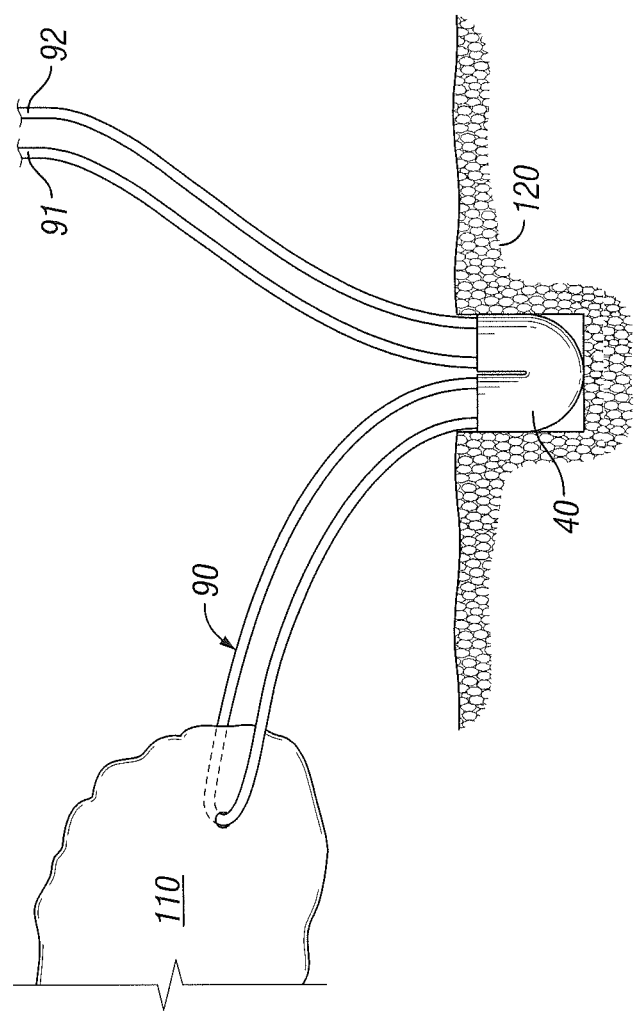
FIG. 4 illustrates yet another step of the method of FIGS. 2 and 3.

FIGS. 3 and 4 collectively illustrate the next step of drawing the length of filament 90 into the first filamentary sleeve 40 by pulling on the filament ends 31 and 32 of shuttle 30 (and ends 51 and 52 of inner filament 50, if present) generally in a proximal direction. As the loop configuration 35 or filament eyelet 55 travels through the first filamentary sleeve 40, a portion of the length of filament 90 ensnared therewith passes through the first end 41 of the first filamentary sleeve 40. Continued tensioning of the first filamentary shuttle 30 pulls the length of filament through the first filamentary sleeve 40 and out of the second end 42 of the first filamentary sleeve 40 until the ends 91 and 92 also exit the first filamentary sleeve 40 through the second end 42, as depicted in FIG. 4. Similar to the tissue engagement step previously described herein, the first and second ends 91, 92 of the length of filament 90 may be and is preferably drawn out of the surgical site for engagement with the second filamentary sleeve 70. Also, similar to the tissue engagement step, the first and second ends 91, 92 may alternatively remain within the surgical site for manipulation therein with the use of an arthroscope or other visualization instrumentation.

With the filamentary sleeve 40 fully deployed prior to this step, it is noted that, commonly, the passageway 43 crushes or compresses along with the entirety of the first filamentary sleeve 40 as the sleeve 40 deploys. Such compression may make it difficult to slide filaments through the passageway 43. In light of this potential issue, the first filamentary shuttle 30 has an equivalent or preferably a larger diameter than the folded length of filament 90. The differences in thickness allow the first filamentary shuttle 40 to act as a larger placeholder within the hollow passageway 43 during deployment, such that a suitably sized passageway can be preserved to provide for simplified passing or shuttling of the filament 90 through the first filamentary sleeve 40, particularly since both ends 91, 92 of the filament are typically doubled over themselves and passed through the first filamentary sleeve 40 (unless filament 190 is used, in which case only the single free end 192 would be doubled over itself). Similarly, the use of the inner filament 50, and eyelet 55, may also provide for simplified passing of the filament 90 into and through the first filamentary sleeve 40 because, with the filament 90 threaded through the eyelet 55 rather than the loop configuration 35, a smaller diameter at the intersection of the filament 90 and inner filament 50 is maintained. This benefit may also be realized relative to first filamentary shuttle 30, which, while not folded onto itself, still has a large diameter.

In one alternative, the filament may arrive to the operator preloaded within the length of the first filamentary sleeve 40. In this variation, first filamentary shuttle 30, or any other shuttle embodiment, is not required. In use, the filament may be utilized to deploy the sleeve in a similar fashion as the filamentary shuttle 30.

Figure 5:
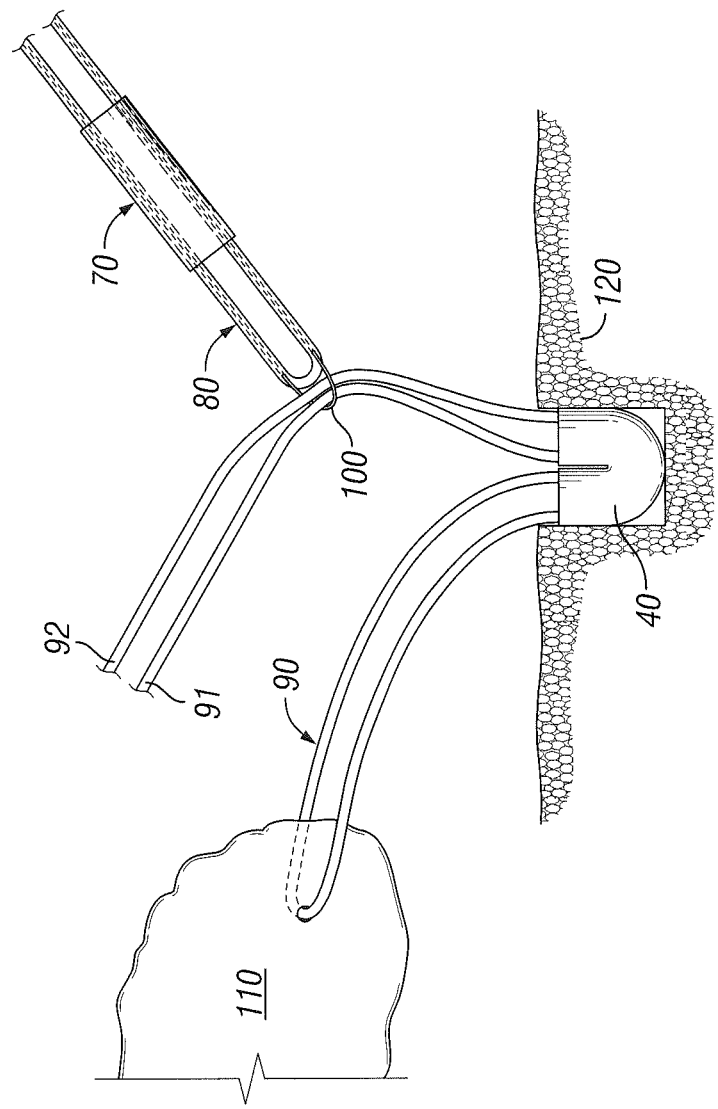
FIG. 5 illustrates a further step in the method of FIGS. 2-4
Figure 6:
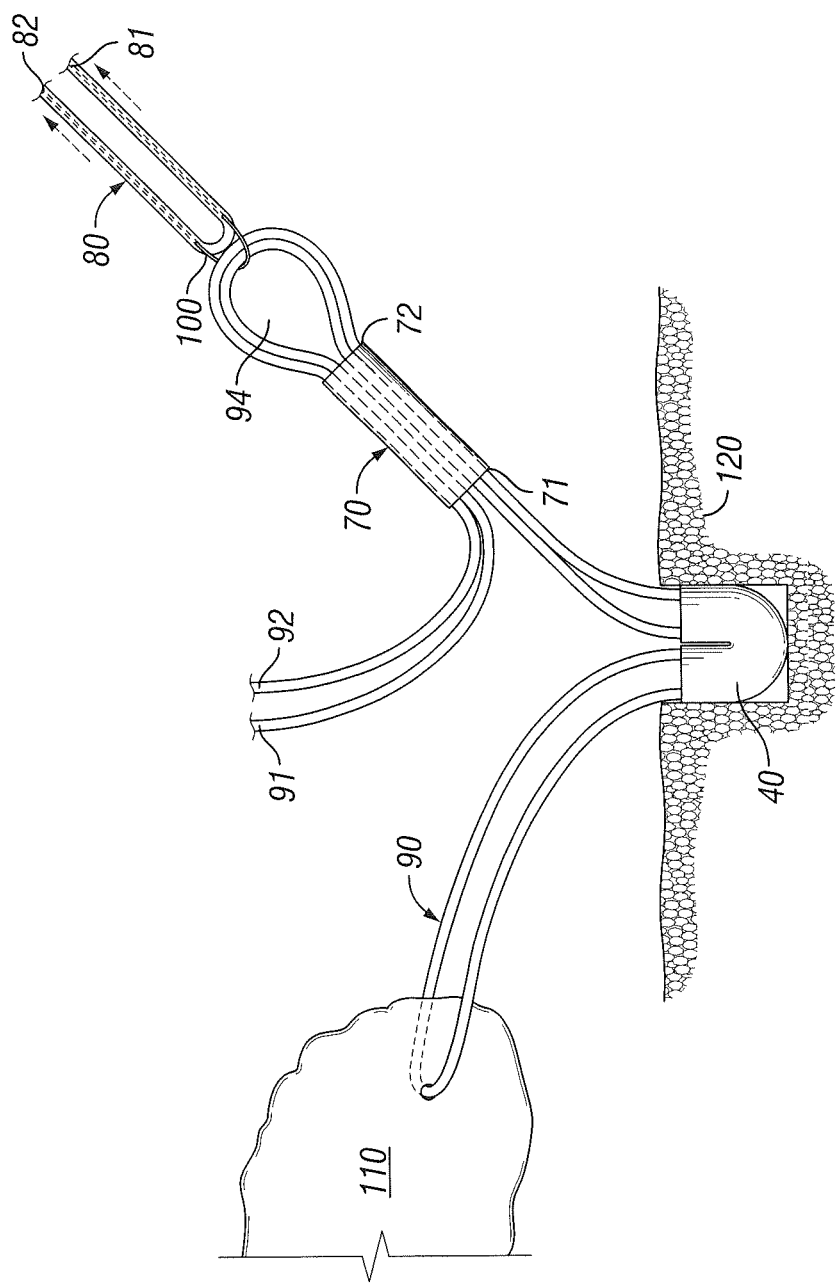
FIG. 6 illustrates a further step in the method of FIGS. 2-5

Referring to FIGS. 4-6, with the length of filament 90 extending through the first filamentary sleeve 40 and the first and second ends 91, 92 extending out of and away from the second end 42 of the first filamentary sleeve 40 and proximal to the surgical site, the length of filament 90 is prepared for engagement with the second filamentary sleeve 70. As such, first and second ends 91, 92 may be threaded through the filament eyelet 105 as depicted in FIG. 5, and as previously mentioned, may be performed proximal to the surgical site.

Thereafter, the second filamentary shuttle ends 81 and 82 may be tensioned in a proximal direction to draw a portion of the length of filament into the second filamentary sleeve as illustrated in FIG. 6. As the loop configuration 85 or filament eyelet 105 travels through the pathway 73 of the second filamentary sleeve 70, a second loop configuration 94 is formed on the length of filament 90, wherein in this position, the length of filament 90 is folded over itself and is positioned through the second filamentary sleeve 70 such that at least a portion of the second loop configuration 94 is positioned outside the second filamentary sleeve 70 and extends away from the second end 72 of the second filamentary sleeve 70, while the free ends 91, 92 oppositely extend from the first end 71 of the second filamentary sleeve 70.

Following the positioning of the length of filament 90 through the second filamentary sleeve 70 to form the second loop configuration 94, the second filamentary shuttle 80, or outer filament 80, may be separated from the inner filament 100 such that the inner filament 100 can be removed from the second loop configuration 94. Alternatively, the inner filament 100 may be simply cut, or, if ends 101 and 102 are accessible, that is, projecting from openings 88 and 89, the operator may simply pull on one of ends 101 or 102 to slide the inner filament 100 from the shuttle and second loop configuration 94, thereby releasing the length of filament 90.

Figure 7:
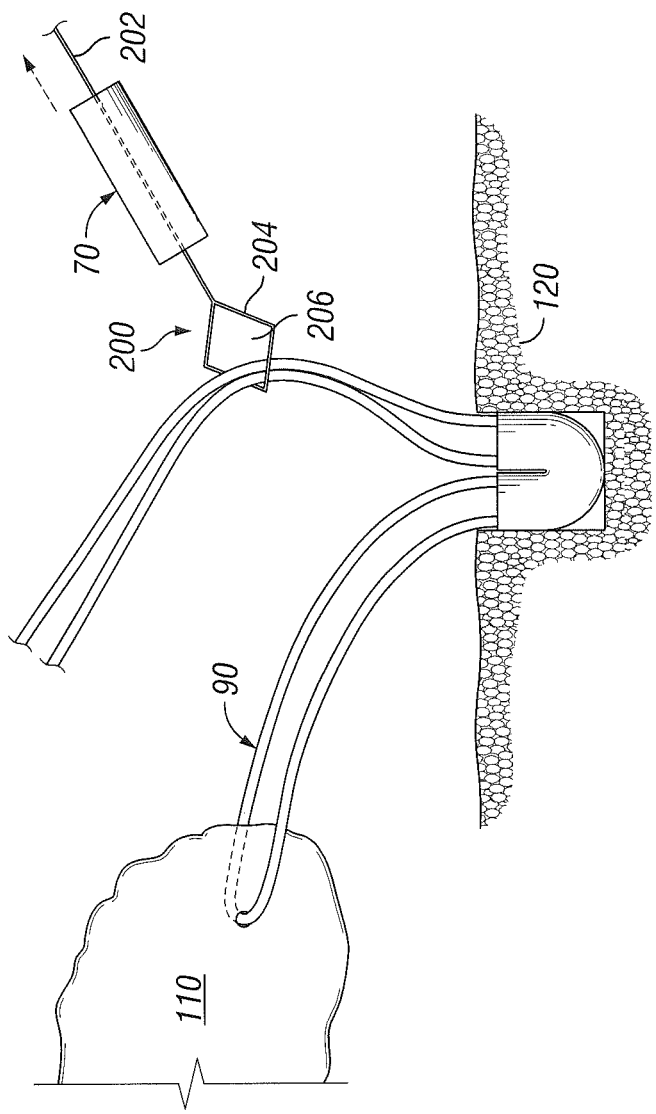
FIGS. 7 and 8 illustrate alternative steps to FIGS. 5 and 6.
Figure 8:
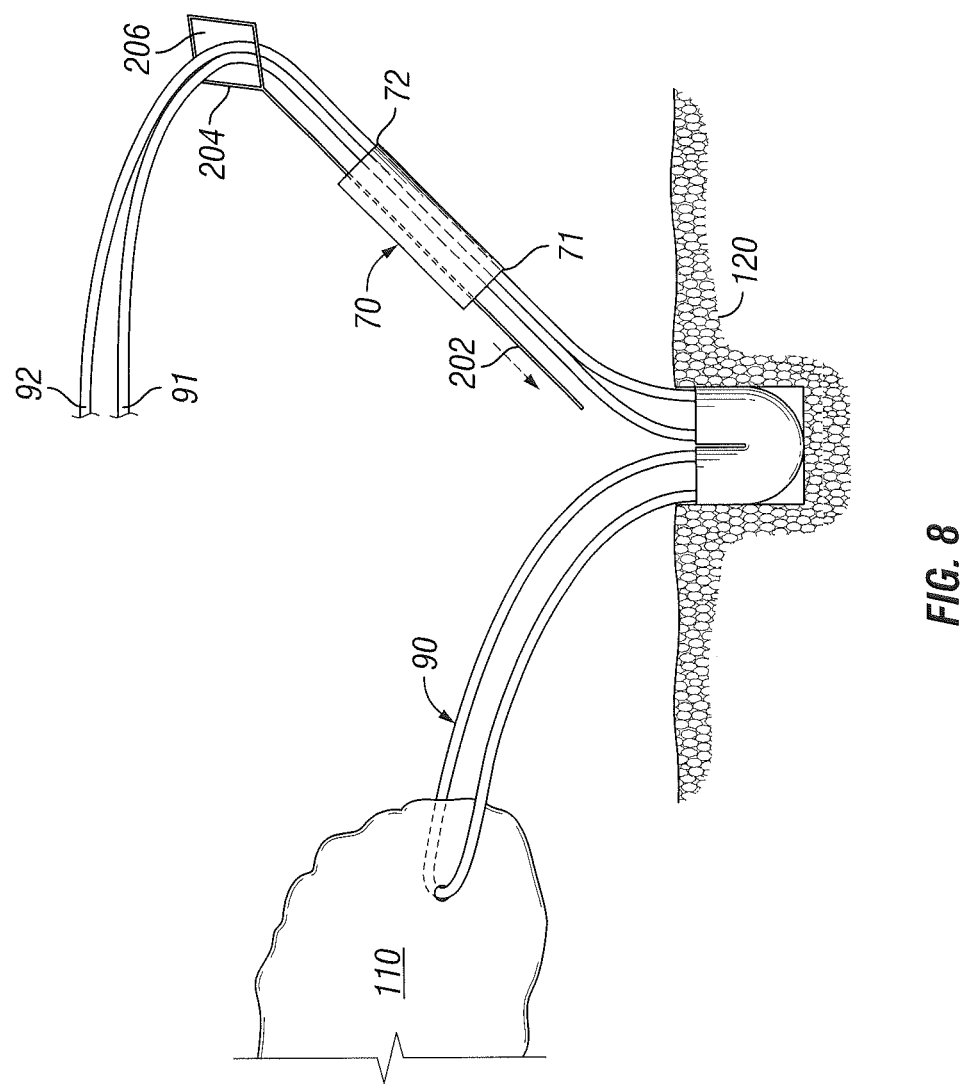

Referring to FIGS. 7 and 8, in an alternative embodiment of the present method, a closed-loop embodiment suture shuttle 200, such as the Nitinol shuttle previously described herein, may be utilized to form the second loop configuration 94. As illustrated in FIG. 7, the first and second ends 91, 92 of the length of filament 90 may be threaded through the closed loop 206 of the head 204, and the elongate shaft 202 may reside within the pathway 73 of the second filamentary sleeve 70. A pulling force may then be applied to the elongate shaft 202 of the suture shuttle 200 in a substantially proximal direction, such as by an actuating instrument (not shown), or simply by manually pulling on the elongate shaft 200. As the head 204 passes through the sleeve 70 or alternatively into a manipulation handle, the head 204 compresses to facilitate movement through the second filamentary sleeve 70 and to facilitate grasping of the length of filament 90. Continued application of the pulling force pulls the first and second ends 91, 92 out of the second filamentary sleeve 70 such that the ends 91, 92 extend away from the second end 72 of the second filamentary sleeve 70.

As illustrated by FIG. 8, with the length of filament 90 remaining within the closed loop 206 or after rethreaded the closed loop 206, the elongate shaft 202 may be passed through the second end 72 and out the first end 71 of the second filamentary sleeve 70. A finger or some other object may be placed along the length of the filament 90 proximal to the second end 72 of sleeve 70 to allow the first and second ends 91, 92 to pass back through the sleeve 70 without the remainder of the filament 90 following therewith, so that the second loop configuration 94 can be formed. Once the first and second ends 91, 92 are passed through the first end 71 of the second filamentary sleeve 70, the ends may be released from the shuttle 200 by sliding the ends 91, 92 back through the closed loop 206 without having to cut the head 204.

While this alternative embodiment has been described with reference to a Nitinol shuttle 200 having a closed-loop configuration that is not opened via cutting or some other mechanism in order to release the filament 90, it is to be understood that the method for forming the second loop via this aforementioned shuttle may be applied to any shuttle that cannot or is not desirable to open in such a manner in order to release the length of filament 90. Otherwise, where it is possible to open the loop, such as filament eyelet 105, it is generally preferably to form the second loop configuration 94 as previously described in relation to the second filamentary shuttle 80.

Figure 9:
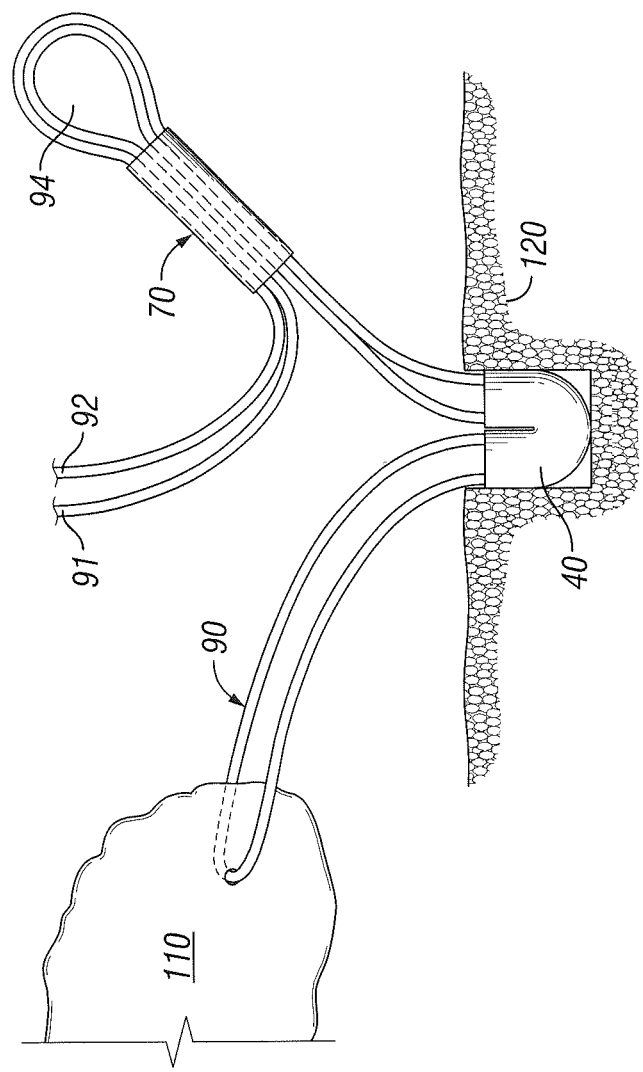
FIG. 9 illustrates an example of the conclusion of the steps illustrated in FIGS. 5 and 6 and FIGS. 7 and 8.
Figure 10:
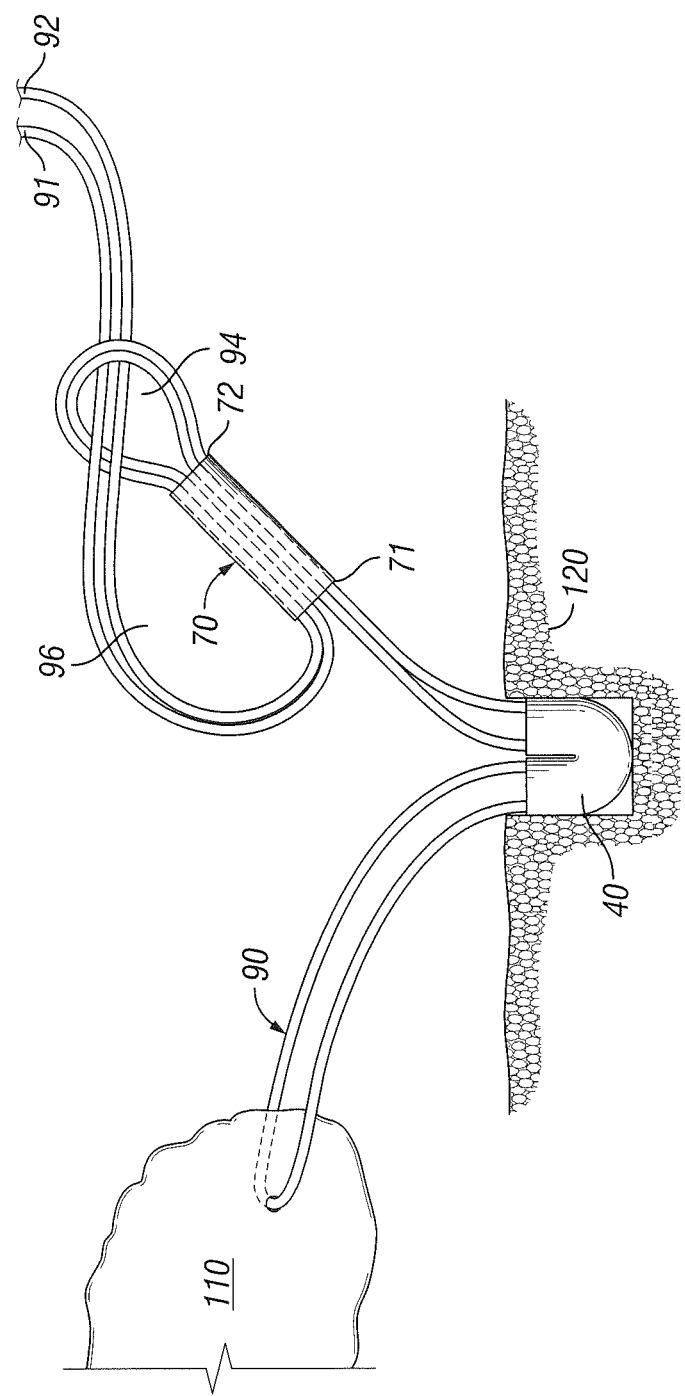
FIG. 10 illustrates a further step of the method embodiment of FIGS. 2-9.

Regardless of which shuttle is utilized to form the second loop configuration 94, an example of the resulting second loop configuration 94 is illustrated by FIG. 9. Again, the second loop configuration 94 may remain within the surgical site or may extend proximally outside of the surgical site towards the operator, which is preferred. In either situation, the free ends 91 and 92 of the length of filament 90 are then maneuvered through the second loop configuration as illustrated in FIG. 10 to form a third loop configuration 96. Collectively, the second filamentary sleeve 70 and second and third loop configuration 94, 96 form a one-way sliding cleat. Such a configuration would also allow for multiple filaments 90 to be positioned in this fashion. Alternatively, if filament 190 (or multiple filaments 190) is utilized, only a single free end 192 of each filament 190 will be passed through a second loop configuration.

Continuing with the example of an arthroscopic surgical procedure, the use of a second filamentary sleeve 70 allows the length of filament 90 to be of standard length. In other words, the use of the second filamentary sleeve 70 to form a one-way sliding cleat does not necessitate an increase in length of the filament 90 such as to require a custom length filament in order to extend out of the surgical site and also form the one-way sliding cleat. Although, alternatively, even in arthroscopic procedures, the loop 94 and free ends 91, 92 may remain within the surgical site.

Figure 11:
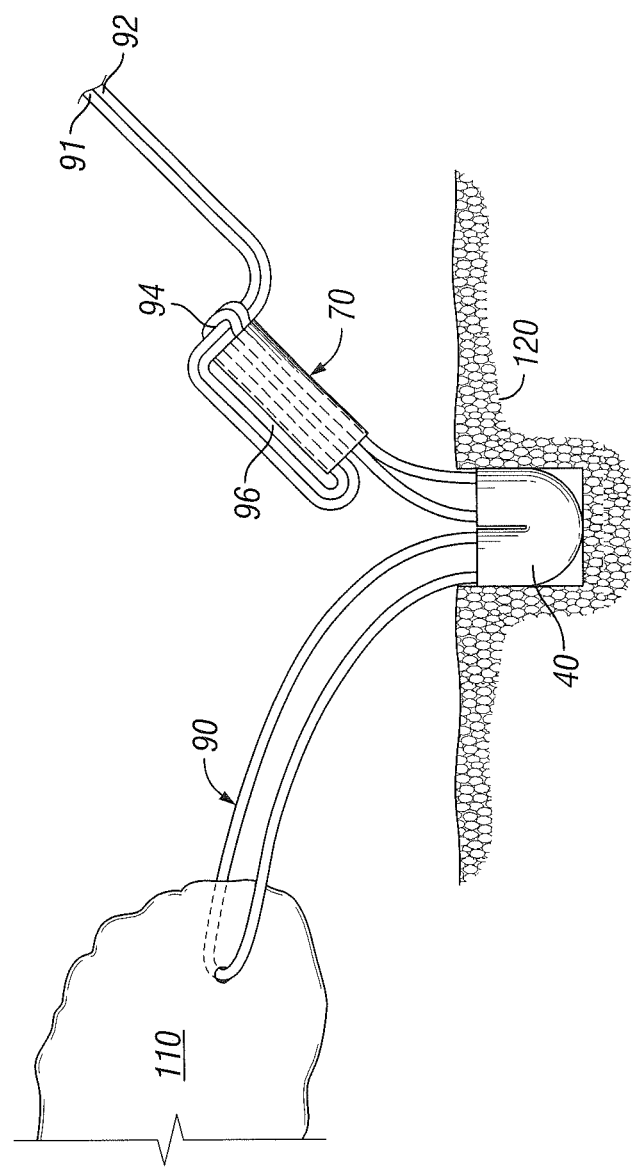
FIG. 11-13 illustrates additional steps of the method of FIGS. 2-10.
Figure 12:
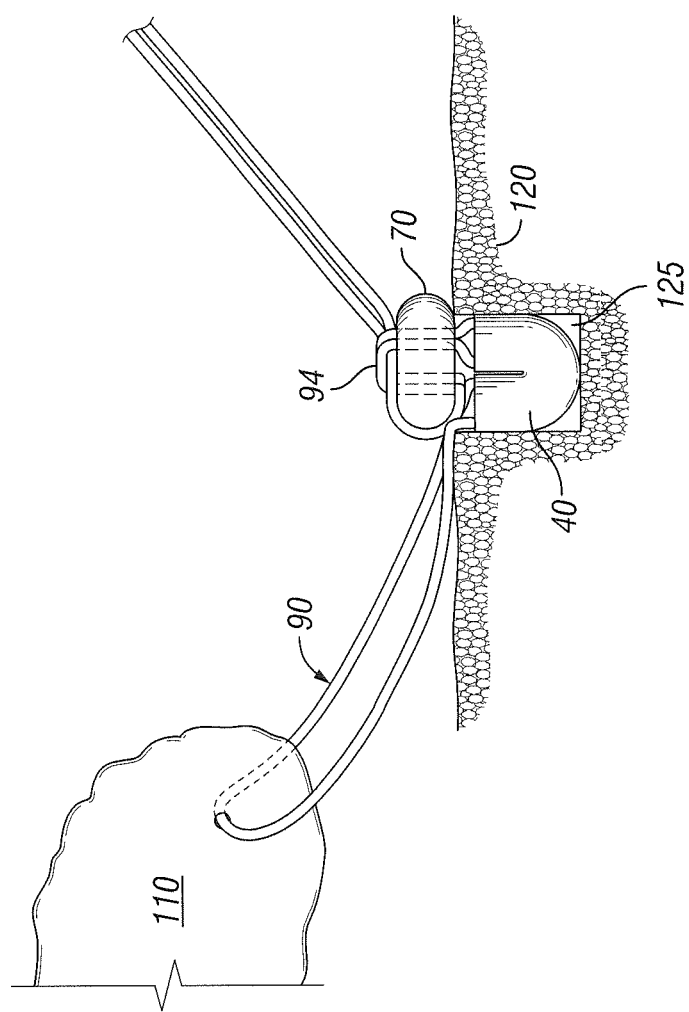

Once the one-way sliding cleat is constructed by forming the second and third loop configurations 94, 96, the second and third loop configurations 94, 96 may be tightened and slid along the filament 90 in conjunction with the second filamentary sleeve 70 into a final fixation position as illustrated in FIGS. 11 and 12. The first and second free ends 91, 92 may be tensioned in a substantially proximal direction while a force may be applied to the third loop configuration 96, or alternatively to the second filamentary sleeve 70, in a substantially distal direction toward the bore hole 125 and first filamentary sleeve 40. The force applied to the third loop configuration 96 may be applied by a knot pusher, or the like, and acts to slide the one-way sliding cleat distally.

The tensioning of the first and second ends 91, 92 not only facilitates sliding of the one-way sliding cleat, the tensioning also facilitates tensioning of the tissue 110. As previously described herein, the passageway 43 may be preserved to allow for the sliding of the filament 90 when the first filamentary sleeve 40 is fully deployed and anchored within the bore hole 125. This slidability through the first filamentary sleeve 40 allows the filament 90 and tissue 110 to be tensioned simultaneously with the sliding of the one-way sliding cleat.

As illustrated in FIG. 12, the one-way sliding cleat is moved into a final fixation position proximal to the first filamentary sleeve 40 such that the second filamentary sleeve 70 partially or completely covers the bore hole 125. In some embodiments, the second filamentary sleeve 70 in the final fixation position sits proud with respect to the bone's surface such that the entirety of the second filamentary sleeve 70 is proximal to the bone's surface. In other embodiments, the entirety of the second filamentary sleeve 70 may enter into the bore hole 125 such that substantially none of the second filamentary sleeve 70 protrudes from the bore hole 125. In yet another embodiment, a portion of the second filamentary sleeve 70 sits proud with respect to the bone's surface, and another portion of the second filamentary sleeve 70 resides within the bore hole 125.

As the one-way sliding cleat moves into the final fixation position, the second and third loop configurations 94, 96 begin to tighten and compress the second filamentary sleeve 70. Depending on the original shape and material construction of the second filamentary sleeve 70, the second filamentary sleeve 70 may deform, such as buckle, flatten, or bulge, from its original configuration into a second configuration. As depicted and exemplified in FIG. 12, the cylindrical second filamentary sleeve 70 bulges into a oblate spheroid or ball-like shape, which lowers the sleeve's profile by generally bringing the first and second ends 71, 72 closer together, serves to more substantially cover the bore hole 125, and facilitates the generation of locking friction along the length of the filament 90 between the second loop configuration 94 and the first end 71 of the second filamentary sleeve 70. Not only does the shape of this second configuration help generate substantial locking friction, but it distributes the normal forces over a relatively large area when compared to normal forces generated by traditional surgical knots, such as a half-hitch, which aids in the prevention of weak points, or areas of high stress, and breakage.

It is envisioned that, if filament 190 is used, it would be easier to utilize multiple filaments 190 (not shown) which may be passed through the tissue 110 at multiple points, as desired based on the position, size and type of tear to the tissue. Each of the filaments 190 may then be positioned through a single combination of first and second filamentary sleeves 40, 70 (or multiple associated combinations of first and second filamentary sleeves 40, 70) and tensioned as above. In another embodiment, such as in a rotator cuff repair, it would be common for multiple filaments 90 (2-4 such filaments, for example) to be shuttled through a single combination of first and second filamentary sleeves 40, 70. For glenoid repair, multiple filaments 90 could be used, though filaments 190 would be preferred as each would include only a single free end 192 doubled over itself within the second filamentary sleeve 70, and thus more filaments 190 may be positioned within a single first and second filamentary sleeve 40, 70 than with multiple filaments 90.

Figure 13:
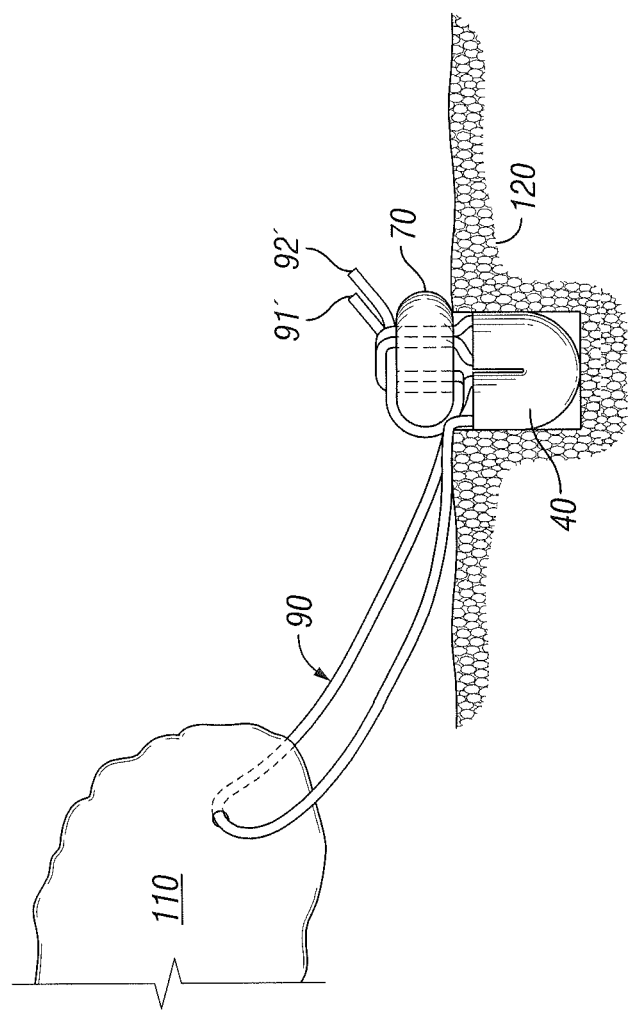

Following sufficient tensioning of the filament 90, the excess portion of the filament free end 192, or free ends 91, 92, may be cut away, as illustrated in FIG. 13, and the surgical site closed, as is known in the art. Such an embodiment can achieve repair and attachment of soft tissue without the need to tie any knots, and thus, the repair is simple to perform for an operator, is free of any knots which may loosen or come untied, and is sufficiently strong to hold the soft tissue in place until the tissue heals to the repair site. Additionally, the suture fixation system 10 allows for the use of standard length filaments 90 by directing the formation of the one-way sliding cleat proximal to the surgical site (e.g., outside the cannula and/or patient and at the operator). Additionally, the tension of the length of filament 90 pulling on the second filamentary sleeve 70 in a substantially distal direction helps counter the tension forces working to pull the first filamentary sleeve 40 out of the bore hole 125 in a substantially proximal direction, thus aiding in a strong anchoring position.

FIG. 13 illustrates the completed configuration of system 10 in which the tissue 110 is secured, reattached, or the like. In maintaining the example of labrum tissue repair, the completed configuration of the system 10, within the glenoid, secures the labrum back against the surface of the glenoid to compress the tissue tear and promote tissue healing.

In one alternative embodiment, the second filamentary sleeve 70 may be substituted by a cylindrical device (not shown) made from rigid yet flexible materials, such as PEEK and Nitinol. Where such an embodiment is utilized in lieu of the second filamentary sleeve 70 and with the first filamentary sleeve 40 implanted and deployed as previously described, the filament 90 may be slid through the cylindrical pathway of the cylindrical device until the cylindrical device either enters the bore hole 125 or sits adjacent the bore hole 125. A crimping apparatus may crimp the cylindrical device, permanently deforming the cylindrical passageway and facilitating the locking of the filament 90 via frictional restraint.

Figure 14:
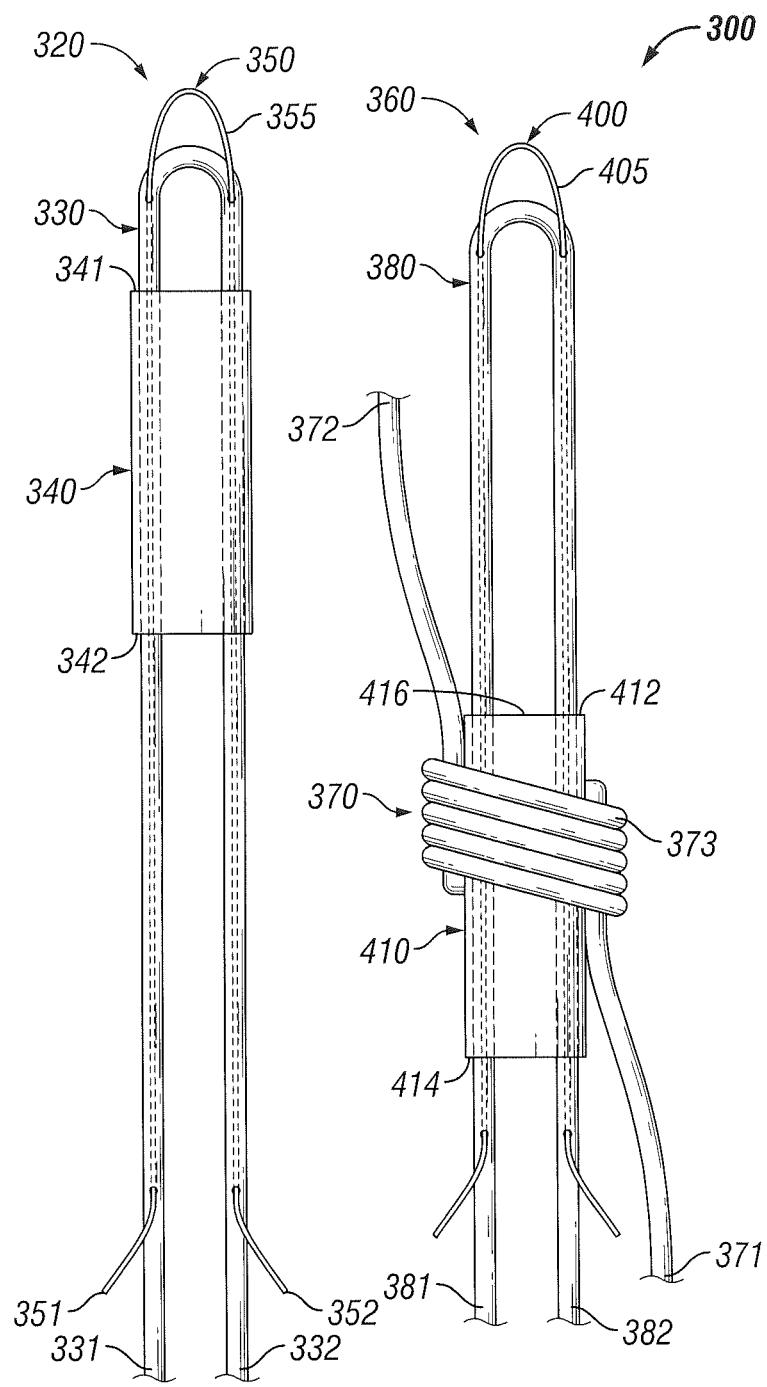
FIG. 14 illustrates an alternative filamentary fixation system embodiment including the first filamentary fixation assembly of FIG. 1 and an alternative embodiment second filamentary fixation assembly.

An alternative system embodiment 300 is depicted in FIG. 14. The system 300 is similar to system 10, but differs with respect to the second filamentary fixation assembly 360. As shown, the filamentary fixation system 300 includes a first filamentary fixation assembly 320 and a second filamentary fixation assembly 360. The first fixation assembly 320 may be identical to the first filamentary fixation assembly 20 previously described, and the repair filament 390 utilized in conjunction with system 300 may be identical to repair filament 90, except in some embodiments, repair filament 390 may be longer than filament 90. Just as with system 10, the filamentary fixation system 300 can be utilized in the repair of damaged tissue, whether that damaged tissue be soft tissue or bone. Additionally, system 300 can be utilized in open surgery and preferably arthroscopic surgery.

Second filamentary fixation assembly 360 generally includes a sliding knot, such as a nail knot, for use within the system 300 in lieu of filamentary sleeve 70. As depicted in FIG. 14, the second filamentary fixation assembly 360 includes a second filamentary shuttle 380, a cylindrical tube 410, and a preformed nail knot 370.

The second filamentary shuttle 380 is depicted as being identical to the second filamentary shuttle 80. However, this depiction is merely exemplary. Any shuttle may be utilized, including the various shuttle embodiments previously disclosed herein in relation to second filamentary fixation assembly 60.

The cylindrical tube 410 generally includes a first end 412 and a second end 414 and a hollow aperture 416 extending therethrough. The cylindrical tube 410 may be constructed from a rigid material, such as polyethylene, for example. However, the cylindrical tube 410 may be flexible and may even be constructed from filamentary material.

The nail knot 370 may be a standard nail knot known in the art that is preformed and loosely engaged to the exterior of the cylindrical tube 410. The nail knot 370 includes free strands 371, 372 that may have sufficient length to be utilized in arthroscopic surgery. The nail knot 370 also includes a plurality of loops 373 that may vary in number. For example, in one embodiment the nail knot may include 2 to 10 loops. In another embodiment, the nail knot may include 4 to 8 loops. In some embodiments, multiple nail knot and cylindrical tube assemblies may be provided in a kit where the nail knot 370 of each assembly has varying lengths and number of loops 373. In another kit embodiment, various other sliding knots, other than nail knots, may be packaged together to provide the operator various functional options.

The second fixation assembly 360 may be provided preassembled such that the nail knot 370 is loosely engaged with an outer surface of the tube 410, and, optionally, the second filamentary shuttle 380 may reside within the tube 410 such that the tube 410 separates the nail knot 370 and the filamentary shuttle 380. Alternatively, the nail knot 370 and tube 410 may be provided separately from the shuttle 380.

Figure 15:
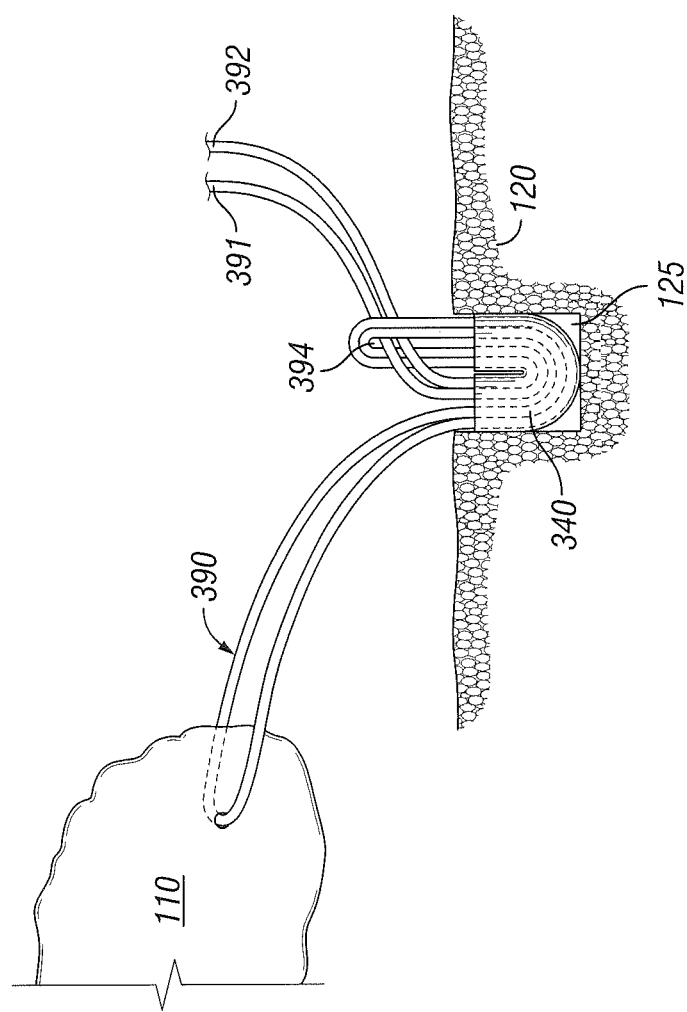
FIG. 15 illustrates a step of one embodiment of the use of the filamentary fixation system of FIG. 14.

FIGS. 15-20 illustrate one embodiment of a method of using filamentary fixation system 300. This method embodiment is similar in certain respects to the first method embodiment as previous disclosed herein. For instance, the presently described method generally includes gaining access to the damaged tissue 110 and the desired bone anchoring location. A bore hole 125 is drilled in the bone 120 and the damaged tissue 110 is engaged with the length of filament 390. The length of filament 390 may also have alternative embodiments similar or identical to filament 190 that allow for a luggage tag configuration. Also the first filamentary sleeve 340 may be positioned and deployed within the bore hole 125 in an identical manner as that previously disclose Unlike the previously disclosed method, a second loop configuration 394 is formed adjacent the first filamentary sleeve 340 in an identical manner to that disclosed in heretofore referenced '804 application. For purposes of clarity, a general summary of forming the second loop configuration 394 as depicted in FIG. 15 is provided. Once the first filamentary sleeve 340 is positioned and deployed within the bore hole 125, the first and second free ends 391, 392 may be threaded through the filament eyelet 355. This step may be performed outside of the surgical site such that the free ends 391, 392 are brought outside the surgical site to filament eyelet 355 prior to threaded engagement with eyelet 355. However, it is envisioned that this step, or any of the steps of this method, may alternatively be performed within the patient and at the surgical site with the assistance of an arthroscope or other viewing instrumentation as known in the art.

Thereafter, the length of filament 390 may be drawn into the first filamentary sleeve 340 by pulling on the filament end 331 and 332 of the shuttle 330 (and ends 351, 352 of inner filament 350, if present). As the filament eyelet 355 travels through the first filamentary sleeve 340, a second loop configuration 394 is formed on the length of filament 390, wherein in this position, the length of filament 390 is folded over itself and is positioned through the sleeve such that at least a portion of the second loop configuration 394 is positioned outside the sleeve at end 342 of the filamentary sleeve 340, and the two or more filament free ends 391, 392 extend through the first filamentary sleeve 340. Continuing with the example of an arthroscopic surgical procedure, the length of filament 390 may have a sufficient length such that the second loop configuration 394 as well as the two filament free ends 391, 392 may extend out of the surgical site proximally through a cannula and to the operator, though alternatively, even in arthroscopic procedures, the loop 394 and free ends 391, 392 may remain within the surgical site.

Following the positioning of the length of filament 390 through the first filamentary sleeve 340, the filamentary shuttle 330, or outer filament 330, may be separated from the inner filament 350 such that the inner filament 350 can be removed from the second loop configuration 394, thereby releasing the length of filament 390. Alternatively, the inner filament 350 may be simply cut, or, if ends 351 and 352 are accessible, the operator may simply pull on one of the ends 351, 352 to slide the inner filament 350 from the shuttle 330 and second loop configuration 394.

Once the filamentary shuttle 330, and optionally inner filament 350, is removed from the second loop configuration 394, the free ends 391, 392 of the length of filament 390 are then maneuvered through the second loop configuration 394, as illustrated by FIG. 15.

Figure 16:
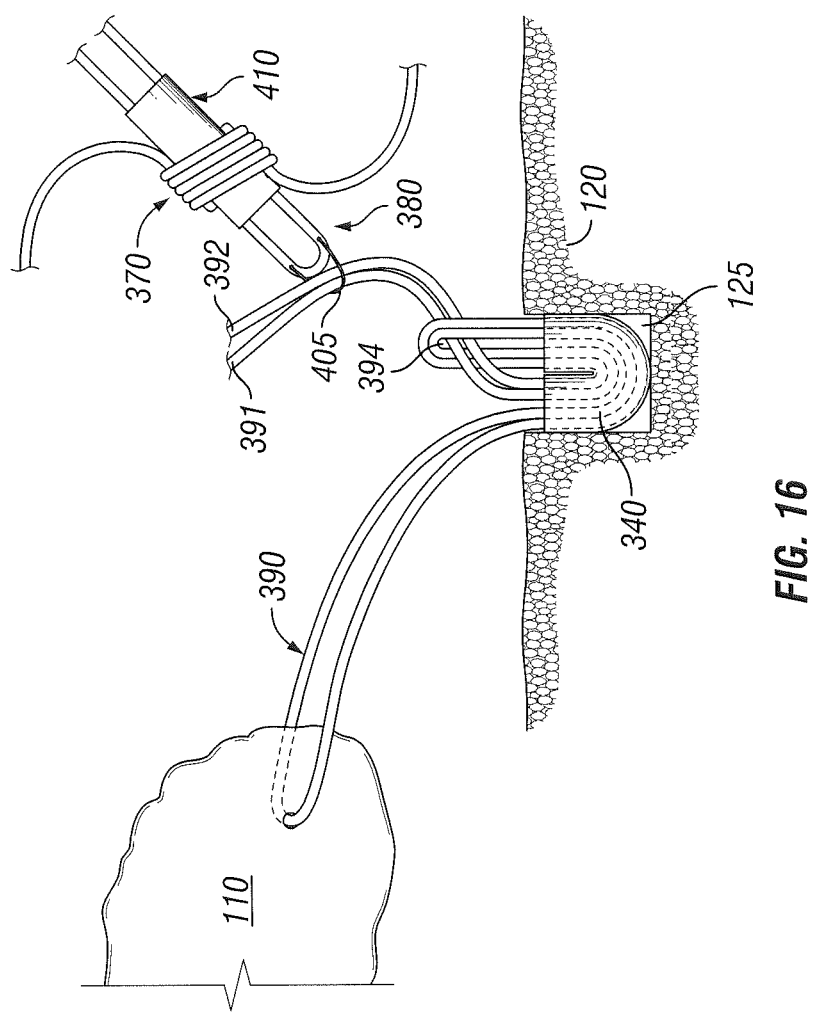
FIG. 16 illustrates another step of the method embodiment of FIG. 15.
Figure 17:
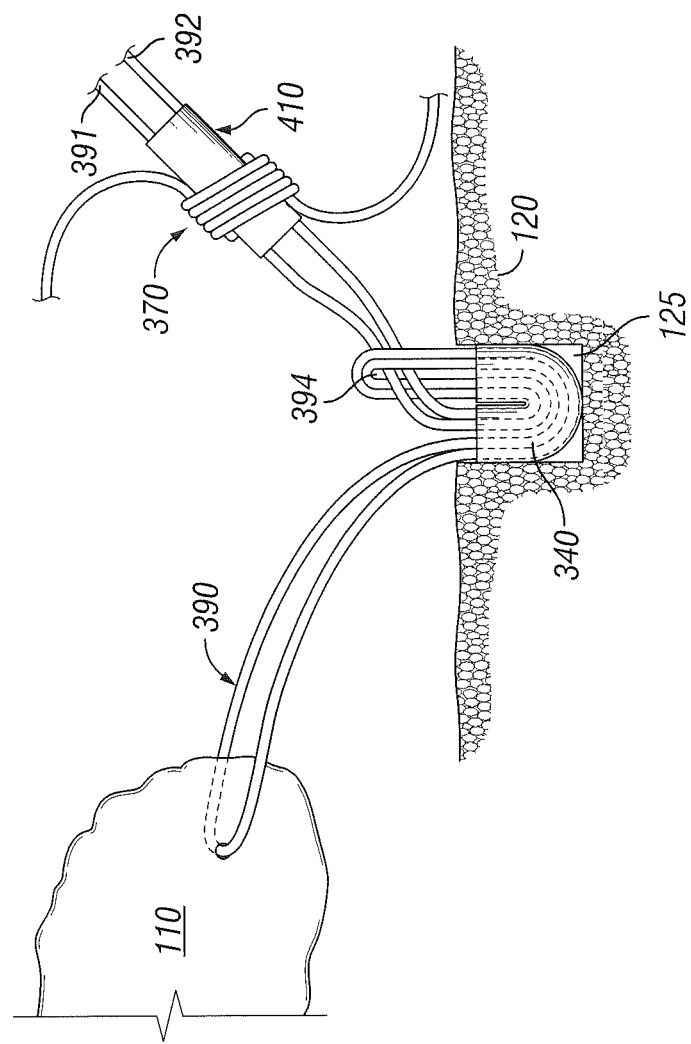
FIG. 17 illustrates yet another step of the method of FIGS. 15 and 16.
Figure 18:
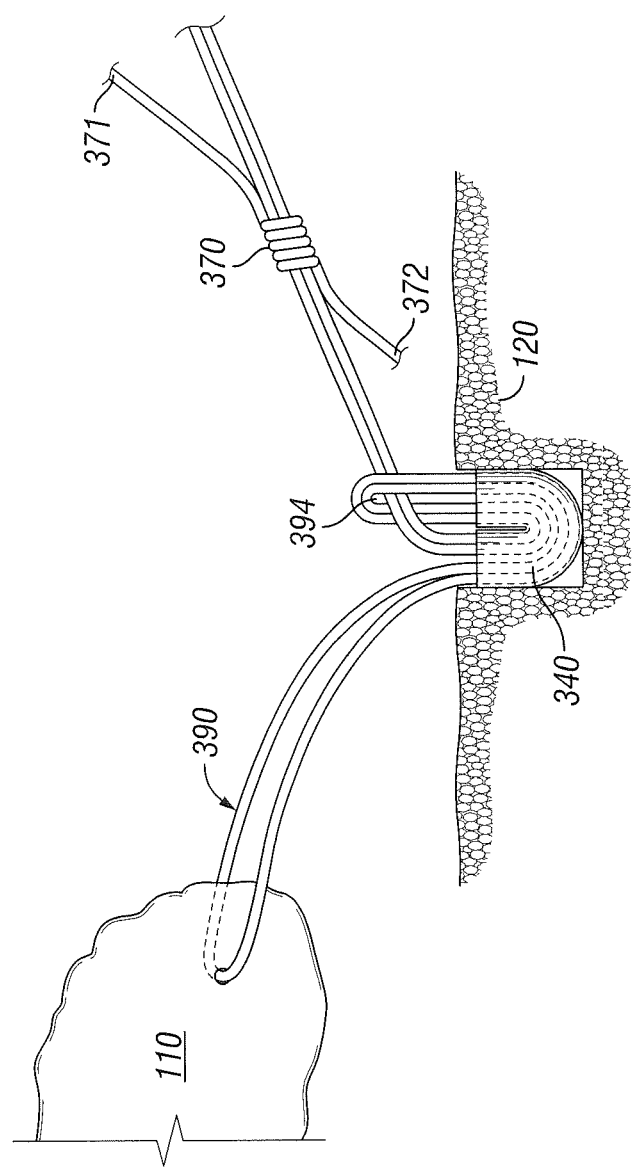
FIG. 18 illustrates a further step in the method of FIGS. 15-17.

Referring to FIGS. 16-18, the first and second free ends 391, 392 may be threaded through the eyelet 405 to ensnare the length of filament 390 that extends from the second loop configuration 394. Thereafter, the ends 381, 382 of the second filamentary shuttle 380 may be tensioned while providing a counterforce to the cylindrical tube 412 to allow for the second filamentary shuttle 380 to pass through the aperture along with the free ends 391, 392. With the free ends 391, 392 extending through the aperture 416 and extending out of the second end of the tube 410, the tube 410 may be separated from the nail knot 370 by sliding the nail knot 370 distally and pulling the tube 410 proximally. This may be performed proximal of the surgical site, or may be performed within the surgical site. However, generally, the operator should have control of the free ends 391, 392 to prevent the nail knot from sliding off the ends 391, 392.

Figure 19:
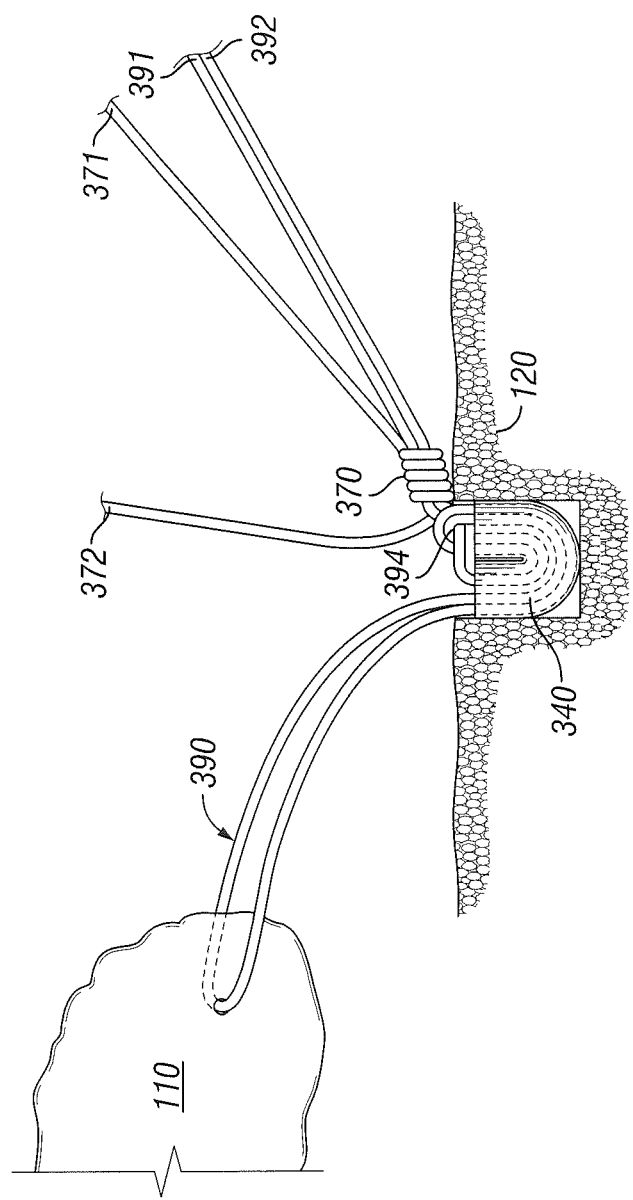
FIG. 19 illustrates an additional step in the method of FIGS. 15-18.

With the nail knot in direct contact with the length of filament 390, the nail knot 370, which at this point should be loose and slidable with respect to the filament 390, can be slid into contact or placed adjacent to the second loop configuration 394, as illustrated in FIG. 19. A tensioner is used to tension free strands 371 and 372 in opposite directions simultaneously causing the nail knot 370 to tighten around the filament 390. The second loop configuration 394 should also be tight and aiding in the prevention of the slackening of the length of filament 390 and the tissue 110. The nail knot 370 provides a redundant locking system to aid in the prevention of tissue slackening while also spreading the locking forces over a larger area to help prevent the formation of stress concentrations that may lead to breakage. Once it is determined that the nail knot 370 is seated in the desired position, the free strands can be cut, as shown in FIG. 20.

Figure 21A:
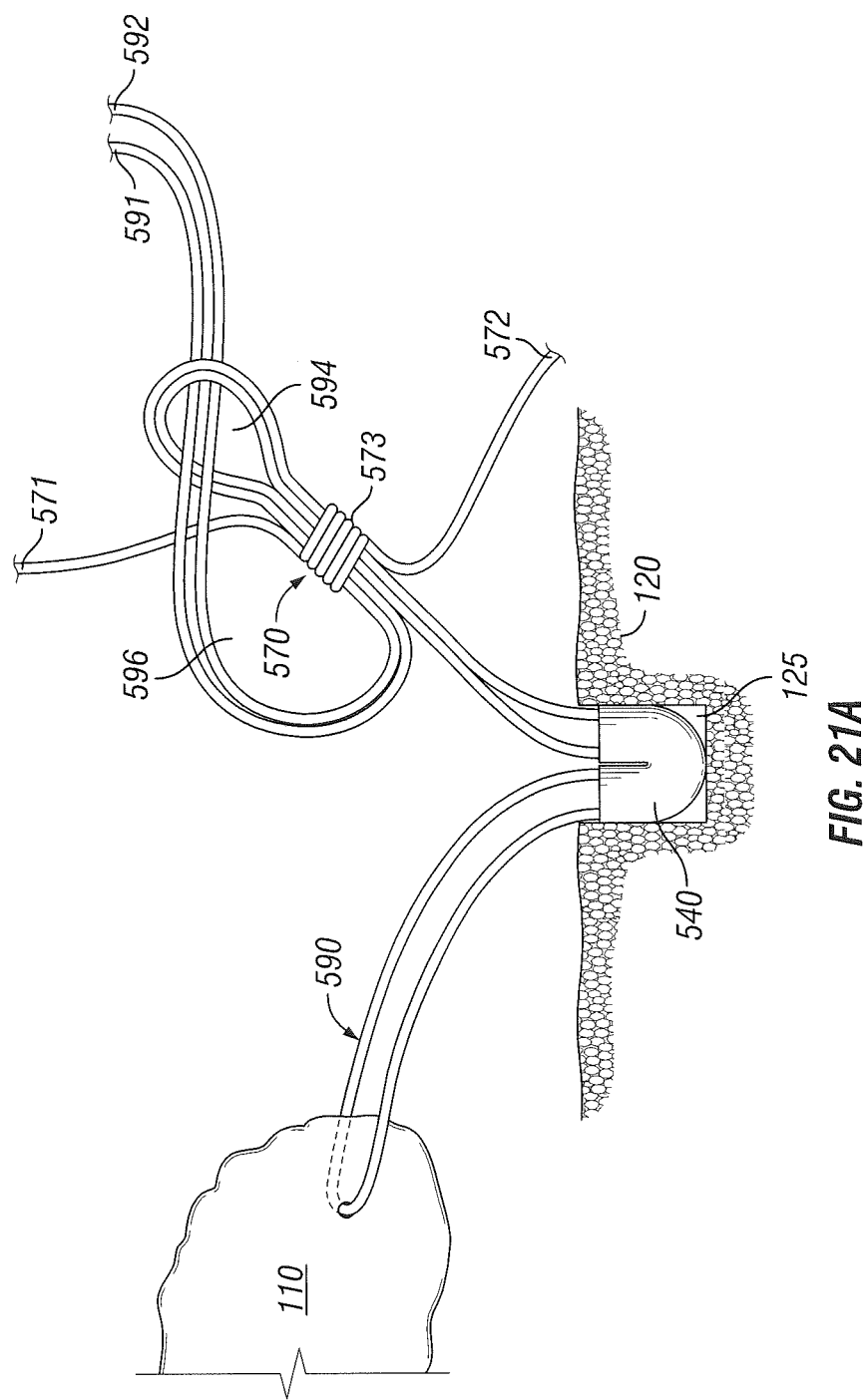
FIGS. 21A and 21B illustrate an alternative method of use.
Figure 21B:
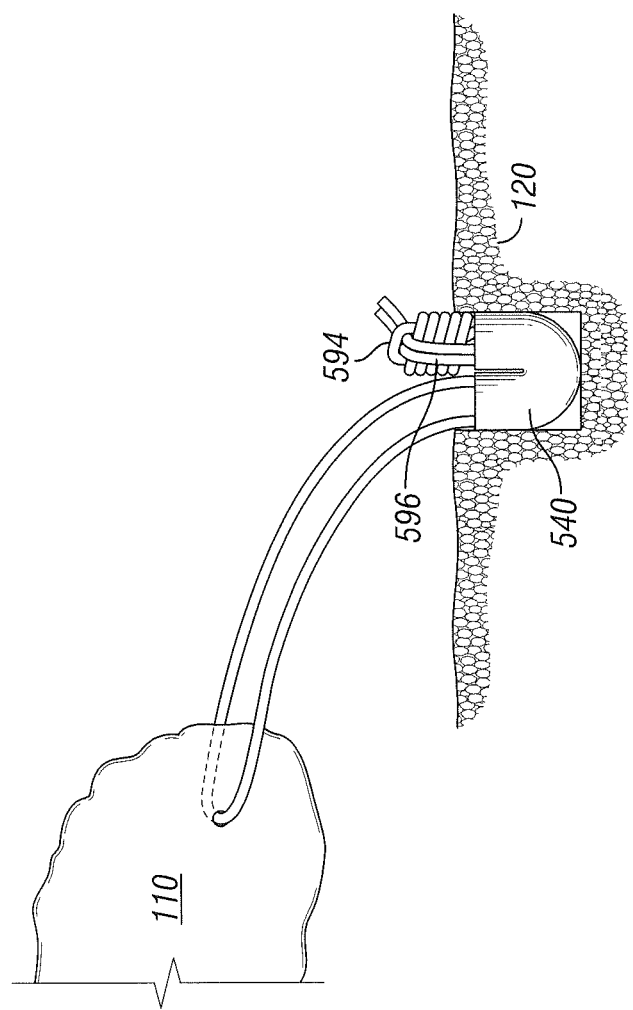

FIGS. 21A and 21B illustrate another embodiment of a method of using a sliding knot. This method embodiment is similar in certain respects to the first method embodiment as previous disclosed herein with respect to FIGS. 2-13, but differs in that this method utilizes a sliding knot in lieu of second filamentary sleeve 70 in the formation of a one-way sliding cleat.

Similar to the first method embodiment, the damaged tissue 110 is accessed either arthroscopically or via open surgery and a bore hole 125 in bone is formed near the damaged tissue 110. A single length of repair filament 590 having a first and second end 591, 592, or alternatively multiple lengths of filament, are passed through or around the damaged tissue 110 in any number of configurations, such as those previously described. A filamentary sleeve 540 is anchored in the bore hole 125, and the first and second ends 591, 592 of the length of filament 590 are passed through the length of the filamentary sleeve 540.

In this position, the first and second ends 591, 592 of the length of filament 590 extend from the first filamentary sleeve 540 and may be threaded through or otherwise captured by a shuttling device, such as filamentary shuttle 380 or the like. The length of filament 590 is then folded over itself at the shuttle engagement location to form a first loop configuration 594. The shuttle and first loop configuration are passed through the loops 573 of a nail knot 570 such that the first loop configuration 594 extends from one end of nail knot 570 and the free ends 591, 592 extend from the other end of nail knot 570. The passage of first loop configuration 594 through the loops 573 of the nail knot 570 can be aided by an optional intermediate guide element, such as cylindrical tube 410, situated between the nail knot 570 and repair filament 590.

With the first loop configuration 594 extending from one end of the nail knot 570, and first and second ends 591, 592 extending from the other end of the nail knot 570, the shuttling device is disengaged from the repair filament 590 and, if present, the intermediate guide element may be withdrawn from the nail knot 570 and repair filament 590. Thereafter, free ends 591 and 592 are passed around the nail knot 570 and through the first loop configuration 594, as depicted in FIG. 21A, to form a second loop configuration 596. The first and second loop configurations 594, 596 and sliding knot 570 form a one-way sliding cleat. In this formation, nail knot 570 is generally loosely and slidably engaged with length of filament 590. It is contemplated that, where the procedure is performed arthroscopically, the one-way sliding cleat may be formed extracorporeally.

Once the one-way sliding cleat is formed, tension can be applied to free ends 591 and 592 and the nail knot 570 can be pushed toward the bore hole 125, such as by a knot pusher. The nail knot free strands 571 and 572 may be sufficiently long such that they extend from the nail knot 570 at a location adjacent the bore hole 125 and extend through an arthroscopic cannula to be retained and manipulated by the operator. As the nail knot 570 reaches the bore hole 125, the nail knot 570 may completely enter into the bore hole 125 and abut the filamentary sleeve 540. In other embodiments, the nail knot 570 may partially enter the bore hole 125 or sit entirely proximal of the bore hole 125. Further tensioning of ends 591 and 592 and further pushing of the nail knot 570 cinches the one-way sliding cleat and tensions the length of filament 590 between the tissue 110 and bore hole 125. The nail knot 570 may be cinched down onto the length of repair filament 590 by tensioning the free strands 571, 572 either concurrently with the final tensioning of ends 591 and 592, or sometime thereafter. The free strands 571, 572 and free ends 591, 592 may then be cut into a final arrangement as depicted in FIG. 21B. The use of a sliding knot in the formation of the one-way sliding cleat facilitates a substantial amount of frictional resistance to help reduce or prevent the slackening of the repair filament.

Figure 22B:
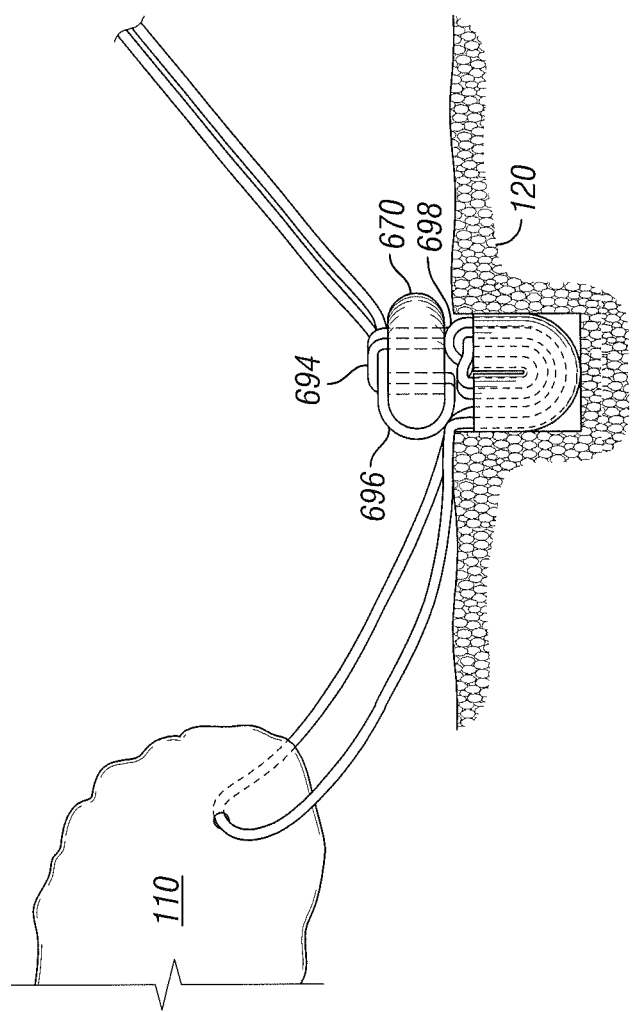

FIGS. 22A and 22B depict an alternative method for securing a length of filament in working communication with tissue. This method combines aspects of the first method embodiment described with respect to FIGS. 2-13 and the second method embodiment described with respect to FIGS. 15-20.

As with all other methods disclosed herein, access to the damaged tissue 110 is gained at the repair site, a bore hole 125 is formed in bone 120, and a length of repair filament 690 is passed through or around tissue 110 such that the repair filament 690 has two free ends 691, 692 extending from the damaged tissue 110. In other embodiments, such as where a luggage tag configuration is utilized, there may be only one free end.

The length of filament 690 may be captured by a first shuttling device (not shown), such as filamentary shuttle 30 or the like, and a first filamentary sleeve 640 is anchored within the bore hole 125. The first filamentary sleeve 640 may be identical to the first filamentary sleeve 40 of filamentary fixation system 10. The repair filament 690 is bent along its length to form a first loop configuration 698 at the shuttle engagement location. The first shuttling device is tensioned and passed, along with the first loop configuration 698, through the length of the first filamentary sleeve 640. Tensioning of the shuttling device is ceased prior to the free ends 691, 692 entering into the filamentary sleeve 640 so that the first loop configuration 698 extends from one end of the first filamentary sleeve 640 and the first and second free ends extend from the other end of the first filamentary sleeve 640. The shuttling device may then be disengaged from the length of filament 690.

The free ends 691, 692 are then passed through the first loop configuration 698 and tensioned. The tensioning of the free ends 691, 692 tightens the first loop configuration 698 around the repair filament 690 passing therethrough and also tensions the repair filament 690 between the tissue 110 and bore hole 125. Thereafter, the free ends 691, 692 may be threaded through or otherwise engaged with a second shuttling device (not shown), such as shuttling device 80 or the like. The repair filament 690 may be bent over itself to form a second loop configuration 694 at the shuttling device engagement location. The second shuttling device is tensioned and passed, along with the second loop configuration 694, through the length of the second filamentary sleeve 670. Tensioning of the second shuttling device is ceased prior to the free ends 691, 692 entering into the second filamentary sleeve 670 so that the second loop configuration 694 extends from one end of the second filamentary sleeve 670 and the first and second free ends 691, 692 extend from the other end of the second filamentary sleeve 670. The second shuttling device may then be disengaged from the repair filament 690.

Thereafter, the free ends 691, 692 are passed around the second filamentary sleeve 670 and through the second loop configuration 694, thereby forming a third loop configuration 696, as depicted in FIG. 22A. The second filamentary sleeve 670 and first and second loop configurations 694, 696 form a sliding-one way cleat. As with many of the methods described herein, it is envisioned that this method may be performed either arthroscopically or via open surgery and that the formation of the sliding-one way cleat may be performed extracorporeally.

Once the one-way sliding cleat is formed, the free ends 691, 692 are tensioned and the second filamentary sleeve pushed, such as by a knot pusher or the like, toward the bore hole 125. As the second filamentary sleeve 670 comes into contact with the bone 120 and/or first filamentary sleeve 640, the second filamentary sleeve 670 compresses such that the ends of the sleeve 670 move closer together and the second and third loop configurations 694, 696 contract.

FIG. 22B illustrates the routing of the repair filament 690 in the final formation. However, it should be understood that this is a schematic representation and that in practice, the repair filament 690 is generally sandwiched tightly between the first and second filamentary sleeves 640, 670, and that the second filamentary sleeve 670 may reside entirely within the bore hole 125. The final configuration facilitates the development of significant friction distributed along the length of the repair filament 690 to reduce localized stress concentrations, help prevent breakage of the repair filament 690, and provide resistance to the slackening of the repair filament 690.

While this method embodiment has been described as utilizing a first and second filamentary sleeve 640, 670, it should be understood that this method may also be performed with a first filamentary sleeve for anchoring to bone and a sliding knot, such as nail knot 570, in lieu of the second filamentary sleeve 670, for forming the one-way sliding cleat. Further, while this and most other embodiments disclose that tensioning of the tissue and the second sleeve occurs simultaneously, each step may be performed individually. For example, the tissue may be tensioned towards the first sleeve and then, once the tissue is tensioned via the filament through the first sleeve, the filament and second sleeve may then be tensioned to finally secure the repair, as discussed above.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for securing a length of filament having two free ends in working communication with tissue, comprising the steps of:
   passing at least one free end of the length of filament through a passageway of a first sleeve;
   implanting the first sleeve into a prepared bore hole in a bone;
   deploying the first sleeve within the bone so as to fixedly secure the first sleeve within the bore hole;
   obtaining a second sleeve formed of a filamentary material having a length along a longitudinal axis, a first end and a second end, and a pathway extending between the first end and second end;
   passing at least a portion of the length of filament through the pathway of the second sleeve such that at least one free end extends from the first end and a loop configuration formed by a portion of the length of filament extends from the second end;
   passing the at least one free end through the loop configuration such that a portion of the length of filament is trapped between the loop configuration and the second end of the second sleeve; and
   tensioning the at least one free end such that the loop configuration travels towards and at least partially into the second sleeve and the second sleeve collapses between its first and second ends, the length of filament is adapted to apply tension to the tissue, and the at least one free end, passed through the loop configuration, is secured within the loop configuration.

2. The method of claim 1, further comprising the step of sliding the second sleeve along the length of filament towards the first sleeve such that at least a portion of the second sleeve is positioned within or over the bore hole.

3. The method of claim 1, wherein the step of passing at least a portion of the length of filament through the pathway of the second sleeve includes:
   passing at least a portion of the length of filament into the second sleeve through the first end, and
   continuing to pull at least a portion of the length of filament through the second sleeve and out the second end, thereby forming the loop configuration on the length of filament outside the second end, wherein in this position, the length of filament is folded over itself, forming the loop configuration at the second end and the at least one free end at the first end.

4. The method of claim 1, wherein the step of passing at least a portion of the length of filament through the pathway of the second sleeve includes:
   pulling the at least one free end through the first end into the pathway and out the second end of the second sleeve, and
   pulling the at least one free end through the second end into the pathway and out the first end such that a portion of the length of filament extends from the second end thereby forming the loop configuration.

5. The method of claim 1, wherein the step of passing the at least one free end through the loop configuration includes forming a one-way sliding cleat wherein the at least one free end extends from the first end of the second sleeve toward the second end of the second sleeve along an outer surface thereof, and through the loop configuration.

6. The method of claim 1, wherein the step of passing at least a portion of the length of filament through the pathway of the second sleeve is performed after the deploying step.

7. A method for securing a length of filament having two free ends, in working communication with both tissue and a tissue anchor, comprising the steps of:
   inserting the tissue anchor into bone;
   obtaining a first sleeve having a length along a longitudinal axis, a first end and second end, and a passageway extending through the first end and second end;
   after the tissue anchor is inserted into bone, pulling at least a portion of the length of filament into the first end of the first sleeve and through the passageway of the first sleeve such that at least one free end extends from the first end and a loop configuration extends from the second end;
   passing the at least one free end through the loop configuration; and
   tensioning the at least one free end to compress the first sleeve.

8. The method of claim 7, wherein the first sleeve is made from one of a filamentary material or a deformable polymer, and
   wherein the step of inserting the tissue anchor into bone comprises inserting the tissue anchor into a prepared bore hole in a bone, and
   further comprising the step of sliding the first sleeve toward the bore hole to a position within or adjacent the bore hole.

9. The method of claim 8, wherein the tissue anchor is a second sleeve having a length along a longitudinal axis thereof, and the step of inserting the second sleeve into the bore hole further comprises inserting the second sleeve into the bore hole such that the second sleeve is folded in the bore hole along its length, and deploying the second sleeve to fixedly secure the second sleeve therein, the second sleeve being disposed between the first sleeve and tissue along the length of filament.

* * * * *